(12) United States Patent
Devengenzo et al.

(10) Patent No.: US 10,182,876 B2
(45) Date of Patent: Jan. 22, 2019

(54) CABLE TENSIONING IN A ROBOTIC SURGICAL SYSTEM

(71) Applicant: Intuitive Surgical Operations, Inc., Sunnyvale, CA (US)

(72) Inventors: Roman L. Devengenzo, Sunnyvale, CA (US); Todd R. Solomon, San Jose, CA (US); Thomas G. Cooper, Menlo Park, CA (US)

(73) Assignee: INTUITIBE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 15/339,244

(22) Filed: Oct. 31, 2016

(65) Prior Publication Data

US 2018/0042688 A1    Feb. 15, 2018

Related U.S. Application Data

(63) Continuation of application No. 14/708,797, filed on May 11, 2015, now Pat. No. 9,486,288, which is a
(Continued)

(51) Int. Cl.
*A61B 34/00* (2016.01)
*G06F 19/00* (2018.01)
(Continued)

(52) U.S. Cl.
CPC .......... *A61B 34/71* (2016.02); *A61B 1/00149* (2013.01); *A61B 34/30* (2016.02); *A61B 34/35* (2016.02); *A61B 34/37* (2016.02); *B25J 9/1045* (2013.01); *G06F 19/00* (2013.01); *G06F 19/3418* (2013.01); *G06F 19/3481* (2013.01); *G16H 40/63* (2018.01); *A61B 90/361* (2016.02); *A61B 2017/00212* (2013.01); *A61B 2017/00477* (2013.01); *A61B 2034/305* (2016.02); *A61B 2034/715* (2016.02); *A61B 2046/234* (2016.02); *Y10T 74/20305* (2015.01)

(58) Field of Classification Search
None
See application file for complete search history.

(56) References Cited

U.S. PATENT DOCUMENTS

| 4,441,695 A | 4/1984 | Watts |
| 4,921,293 A | 5/1990 | Ruoff et al. |

(Continued)

FOREIGN PATENT DOCUMENTS

JP    2002266962 A    9/2002

OTHER PUBLICATIONS

Co-pending U.S. Appl. No. 08/517,053, filed Aug. 21, 1995.
(Continued)

*Primary Examiner* — Mussa A Shaawat
*Assistant Examiner* — Kyung J Kim

(57) ABSTRACT

A termination assembly of a cabling system in a robotic surgical manipulator comprises a block including first and second cable pathways sized for receipt of a first cable. The first cable pathway includes a first retainer sized to prevent passage of a first fitting coupled to the first cable. The termination assembly also includes a first support coupled to the block and around which the first cable is routed.

20 Claims, 21 Drawing Sheets

Related U.S. Application Data continuation of application No. 11/613,578, filed on Dec. 20, 2006, now Pat. No. 9,050,119.

(60) Provisional application No. 60/752,755, filed on Dec. 20, 2005.

(51) Int. Cl.

| | | |
|---|---|---|
| *B25J 9/10* | (2006.01) | |
| *A61B 34/35* | (2016.01) | |
| *A61B 1/00* | (2006.01) | |
| *A61B 34/30* | (2016.01) | |
| *A61B 34/37* | (2016.01) | |
| *G16H 40/63* | (2018.01) | |
| *A61B 17/00* | (2006.01) | |
| *A61B 46/23* | (2016.01) | |
| *A61B 90/00* | (2016.01) | |

(56) References Cited

U.S. PATENT DOCUMENTS

| | | | |
|---|---|---|---|
| 5,176,581 A | 1/1993 | Kumm | |
| 5,193,963 A * | 3/1993 | McAffee | B25J 3/04 |
| | | | 414/5 |
| 5,730,578 A | 3/1998 | Smidler | |
| 5,800,423 A | 9/1998 | Jensen | |
| 5,807,377 A | 9/1998 | Madhani et al. | |
| 5,931,832 A | 8/1999 | Jensen | |
| 5,957,423 A | 9/1999 | Kronner | |
| 5,976,122 A | 11/1999 | Madhani et al. | |
| 6,007,243 A | 12/1999 | Ergun et al. | |
| 6,132,368 A | 10/2000 | Cooper | |
| 6,206,903 B1 | 3/2001 | Ramans | |
| 6,246,200 B1 | 6/2001 | Blumenkranz et al. | |
| 6,331,181 B1 | 12/2001 | Tierney et al. | |
| 6,474,125 B1 | 11/2002 | Denis et al. | |
| 6,491,701 B2 | 12/2002 | Tierney et al. | |
| 6,574,355 B2 | 6/2003 | Green | |
| 6,770,081 B1 | 8/2004 | Cooper et al. | |
| 6,786,896 B1 | 9/2004 | Madhani et al. | |
| 6,962,570 B2 | 11/2005 | Callanan et al. | |
| 9,050,119 B2 | 6/2015 | Devengenzo et al. | |
| 2003/0218252 A1 | 11/2003 | Suzuki et al. | |
| 2003/0221504 A1 | 12/2003 | Stoianovici et al. | |
| 2005/0021050 A1 | 1/2005 | Cooper | |
| 2005/0023424 A1 | 2/2005 | Chow et al. | |
| 2006/0106369 A1 | 5/2006 | Desai et al. | |
| 2006/0161136 A1 | 7/2006 | Anderson et al. | |
| 2006/0161137 A1 | 7/2006 | Orban, III | |
| 2006/0161138 A1 | 7/2006 | Orban, III | |
| 2006/0167440 A1 | 7/2006 | Cooper et al. | |
| 2006/0235436 A1 | 10/2006 | Anderson et al. | |
| 2007/0055289 A1 | 3/2007 | Scouten et al. | |
| 2007/0119274 A1 | 5/2007 | Devengenzo et al. | |
| 2007/0137371 A1 | 6/2007 | Devengenzo et al. | |
| 2007/0137372 A1 | 6/2007 | Devengenzo et al. | |
| 2007/0142824 A1 | 6/2007 | Devengenzo et al. | |
| 2015/0238267 A1 | 8/2015 | Devengenzo et al. | |

OTHER PUBLICATIONS

Co-pending U.S. Appl. No. 60/752,755, filed Dec. 20, 2005.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

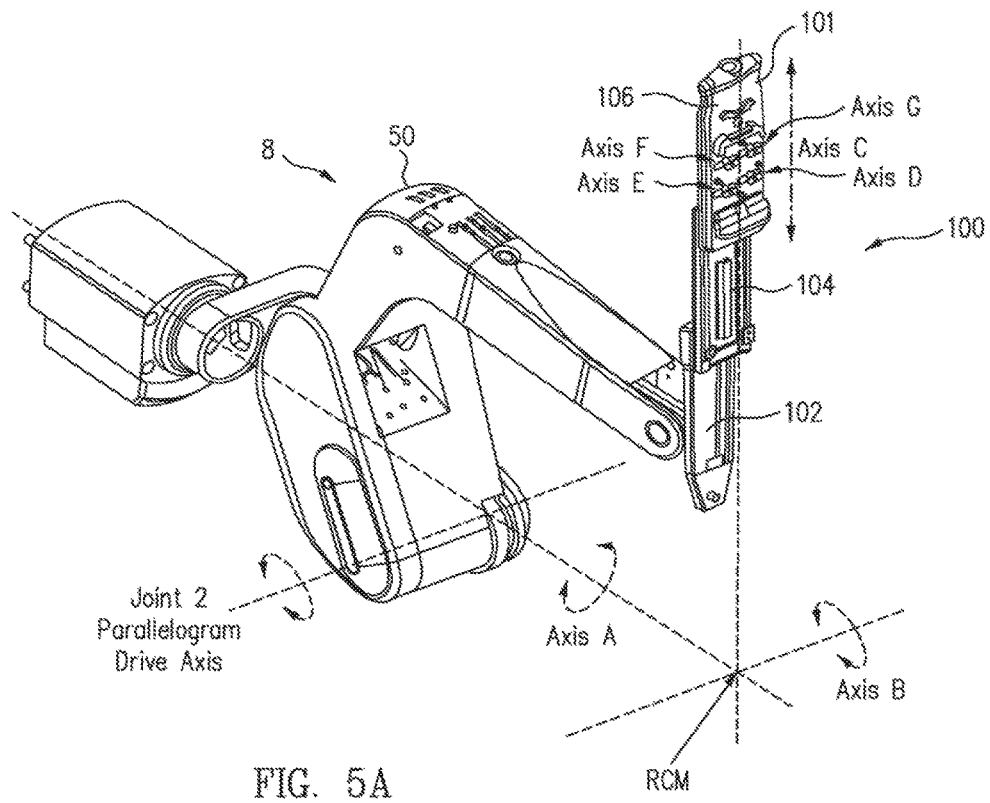
FIG. 5A
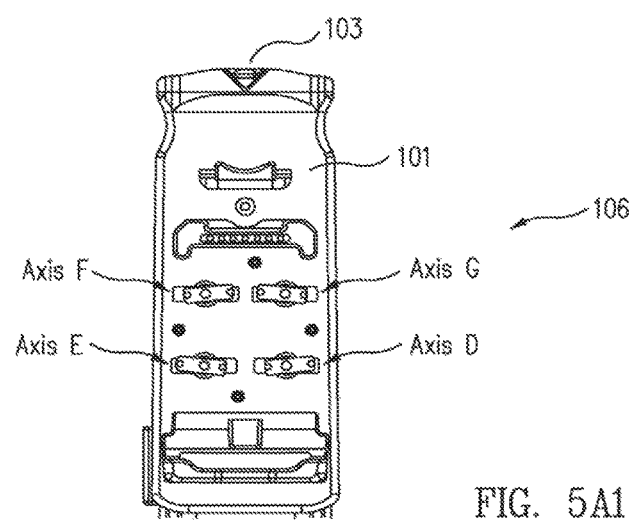
FIG. 5A1

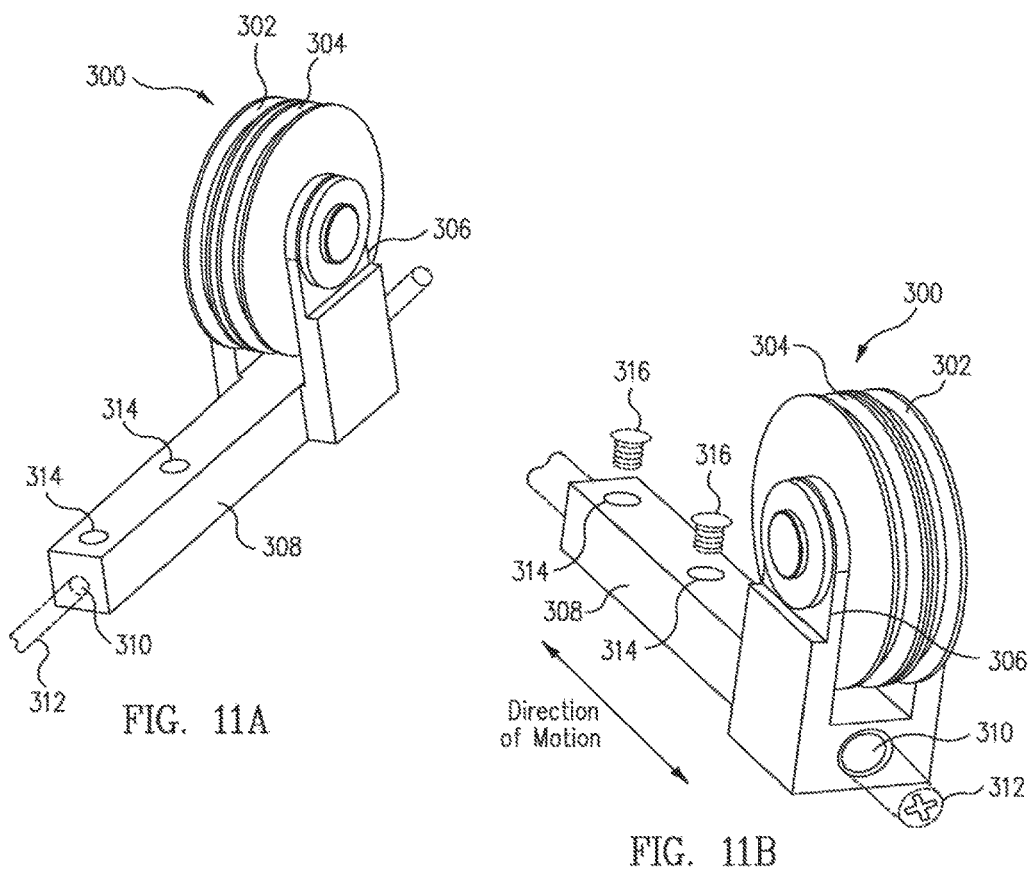
FIG. 11A
FIG. 11B
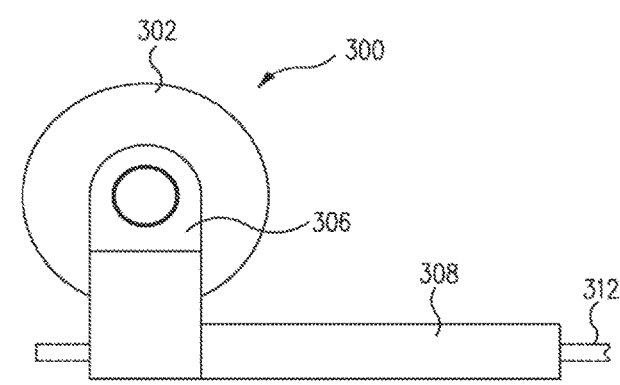
FIG. 11C

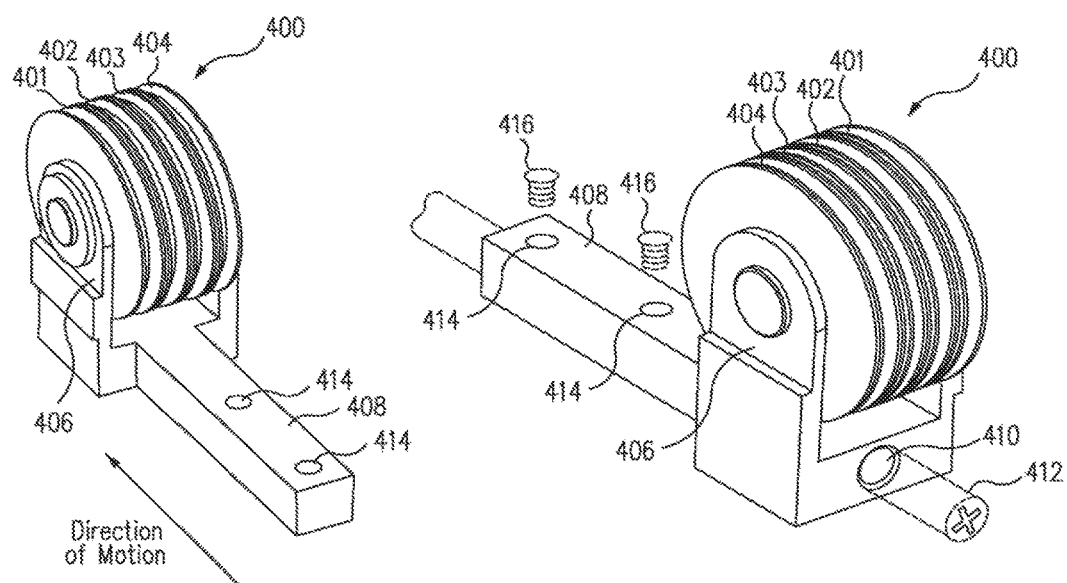
FIG. 12A
FIG. 12B
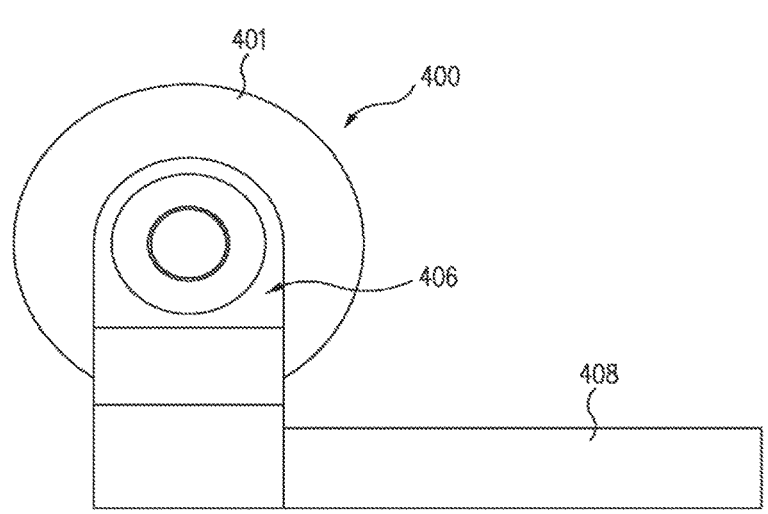
FIG. 12C

CABLE TENSIONING IN A ROBOTIC SURGICAL SYSTEM

CROSS-REFERENCE TO RELATED APPLICATIONS

This application is a continuation of U.S. patent application Ser. No. 14/708,797, filed May 11, 2015; which is a continuation of U.S. patent application Ser. No. 11/613,578, filed Dec. 20, 2006; which claims the benefit of U.S. Provisional Application No. 60/752,755, filed Dec. 20, 2005, the full disclosures of which (including all references incorporated by reference therein) are incorporated by reference herein for all purposes.

This application is related to U.S. application Ser. No. 11/613,800, filed Dec. 20, 2006, entitled "Telescopic Insertion Axis Of A Robotic Surgical System", U.S. application Ser. No. 11/556,484, filed Nov. 3, 2006, entitled "Indicator For Tool State and Communication In A Multi-Arm Robotic Telesurgery", U.S. application Ser. No. 11/613,695, filed Dec. 20, 2006, entitled "Instrument Interface In A Robotic Surgical System", and U.S. application Ser. No. 11/613,915, filed Dec. 20, 2006, entitled "Wireless Communication In A Robotic Surgical System", the full disclosures of which (including all references incorporated by reference therein) are incorporated by reference herein for all purposes.

TECHNICAL FIELD

The present invention relates generally to surgical robot systems and, more particularly, to an apparatus, system, and method for cable tensioning in a robotic surgical system.

BACKGROUND

Minimally invasive robotic surgical or telesurgical systems have been developed to increase a surgeon's dexterity and to avoid some of the limitations on traditional minimally invasive techniques. In telesurgery, the surgeon uses some form of remote control, e.g., a servomechanism or the like, to manipulate surgical instrument movements, rather than directly holding and moving the instruments by hand. In telesurgery systems, the surgeon can be provided with an image of the surgical site at the surgical workstation. While viewing a two or three dimensional image of the surgical site on a display, the surgeon performs the surgical procedures on the patient by manipulating master control devices, which in turn control motion of the servomechanically operated instruments.

In robotically-assisted surgery, the surgeon typically operates a master controller to control the motion of surgical instruments at the surgical site from a location that may be remote from the patient (e.g., across the operating room, in a different room, or a completely different building from the patient). The master controller usually includes one or more hand input devices, such as hand-held wrist gimbals, joysticks, exoskeletal gloves or the like, which are operatively coupled to the surgical instruments that are releasably coupled to a patient side surgical manipulator ("the slave"). The master controller controls the instruments' position, orientation, and articulation at the surgical site. The slave is an electro-mechanical assembly which includes a plurality of arms, joints, linkages, servo motors, etc., that are connected together to support and control the surgical instruments. In a surgical procedure, the surgical instruments (including an endoscope) may be introduced directly into an open surgical site or more typically through trocar sleeves into a body cavity. Depending on a surgical procedure, there are available a variety of surgical instruments, such as tissue graspers, needle drivers, electrosurgical cautery probes, etc., to perform various functions for the surgeon, e.g., holding or driving a needle, suturing, grasping a blood vessel, or dissecting, cauterizing or coagulating tissue.

A surgical manipulator assembly may be said to be divided into three main components that include a non-sterile drive and control component, a sterilizable end effector or surgical tool/instrument, and an intermediate connector component. The intermediate connector component includes mechanical elements for coupling the surgical tool with the drive and control component, and for transferring motion from the drive component to the surgical tool. Cables (also referred to as wire rope) and pulleys in conjunction with motors have been used to actuate carriages, the surgical instrument, and other apparatus of the surgical system. Prior telerobotic surgical systems with such pulley systems are described for example in U.S. application Ser. Nos. 08/517,053 and 11/314,040, the complete disclosures of which are incorporated herein by reference for all purposes.

Setting and maintaining cable tension is of prime importance for accurately and precisely moving the various apparatus and instruments during surgery. Previously, cable tension was set by screw clamps at the termination points of the cables. Setting the cable tension using these screw clamps required skill beyond that of standard field personnel.

What is needed, therefore, are improved apparatus and methods for setting cable tension in a telerobotic surgical system for remotely controlling surgical instruments at a surgical site on a patient. In particular, these apparatus and methods should allow for easily adjusting cable tension using standard tools. Accordingly, a cable tensioning apparatus, system, and method having improved efficiency and cost-effectiveness is highly desirable.

SUMMARY

The present invention provides an apparatus, system, and method for setting, maintaining, and adjusting cable tension in a telerobotic surgical system. In particular, an adjustable cable tensioning apparatus, a termination block, and a method of cable tensioning in a closed loop cable scheme are provided.

In accordance with an embodiment of the present invention, an apparatus for cable tensioning comprises an arm, a pulley rotatably coupled to the arm, and a base operably coupled to the arm, the base including a translation mechanism for changing the position of the pulley to control a tension of a cable movable along the pulley.

In accordance with another embodiment of the present invention, a robotic surgical system is provided, the system comprising a drive assembly, a surgical instrument, and a manipulator arm operably coupling the surgical instrument to the drive assembly, the manipulator arm having a cable tensioning apparatus as described above. The system further includes a cable running along the pulley for transmitting motion from the drive assembly to the manipulator arm, the tension of the cable being controlled in part by the cable tensioning apparatus.

In accordance with another embodiment of the present invention, a method of cable tensioning is provided, the method comprising providing a drive assembly, providing a surgical instrument, providing a manipulator arm as described above operably coupling the surgical instrument to the drive assembly. The method further includes moving a cable along the pulley for transmitting motion from the drive assembly to the manipulator arm, and changing the position of the pulley to control the tension of the cable.

In accordance with yet another embodiment, a termination block of a cabling system in a robotic surgical manipulator is provided, the termination block comprising a block including two cable pathways, each cable pathway including a retaining means for a ball fitting, and a support for moving a cable along the two cable pathways, the cable including a ball fitting in each of the cable pathways.

Advantageously, the present invention provides for easily adjusting cable tension in a robotic surgical arm and system, for example using standard tools and/or a processor, and also provides for a safety feature based upon cable redundancy in a termination block.

The scope of the invention is defined by the claims, which are incorporated into this section by reference. A more complete understanding of embodiments of the present invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIGS. 5A through 5E are perspective views of a manipulator including a telescopic insertion axis and cable tensioning means in accordance with an embodiment of the present invention. FIG. 5A1 is a close-up view of a carriage link of the telescopic insertion axis in accordance with an embodiment of the present invention.

FIGS. 11A through 11D are different views of a dual linear tensioning apparatus in accordance with another embodiment of the present invention.

FIGS. 12A through 12C are different views of a quad linear tensioning apparatus in accordance with another embodiment of the present invention.

Figure 1:
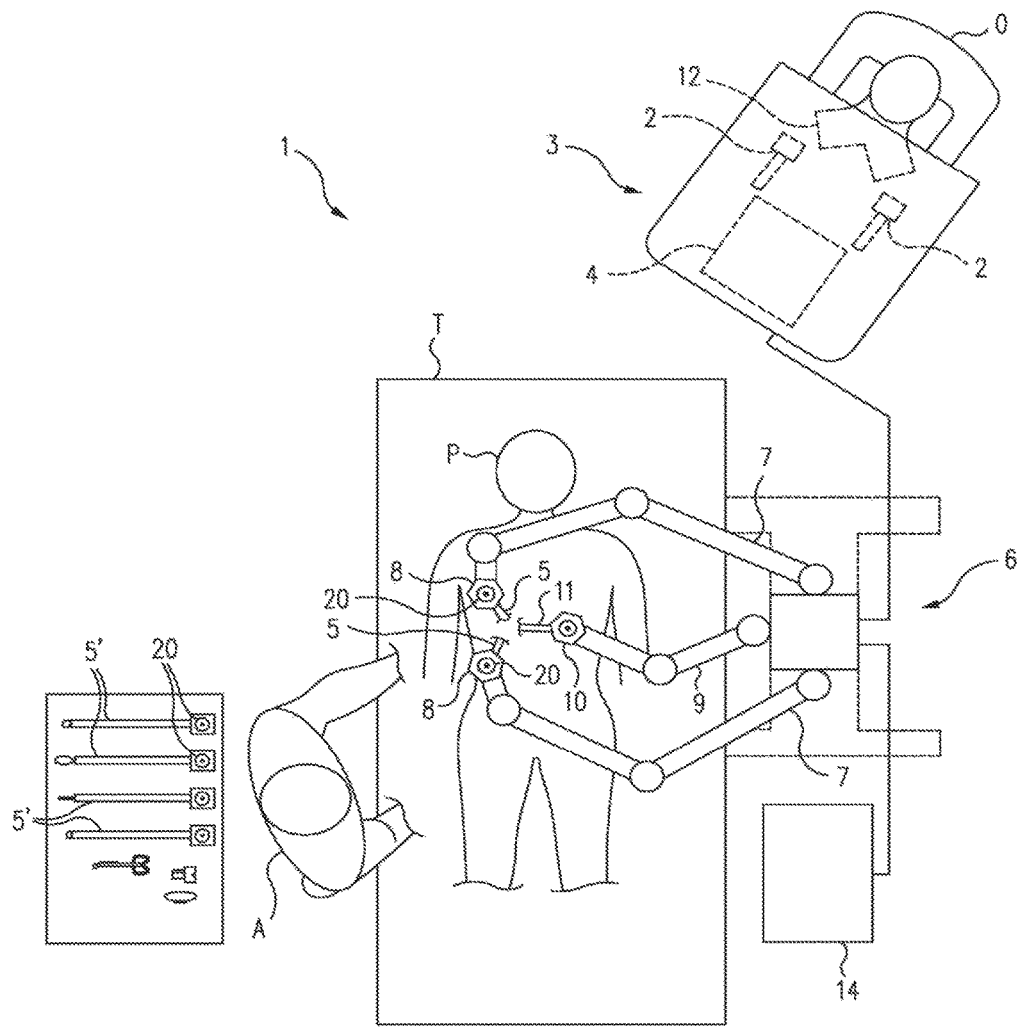
FIG. 1 is a schematic plan view of a portion of an operating theater illustrating a robotic surgical system, including a master surgeon console or workstation for inputting a surgical procedure and a robotic manipulator system for robotically moving surgical instruments at a surgical site within a patient.

Embodiments of the present invention and their advantages are best understood by referring to the detailed description that follows. It should be appreciated that like reference numerals are used to identify like elements illustrated in one or more of the figures. It should also be appreciated that the figures may not be necessarily drawn to scale.

DETAILED DESCRIPTION

The present invention provides an apparatus and method for setting, maintaining, and/or adjusting cable tension in a telerobotic surgical system, the cable tensioning apparatus in one embodiment including an arm having a first end and a second end, a pulley rotatably coupled to the first end of the arm, and a base operably coupled to the second end of the arm, the base including a translation mechanism for changing the position of the pulley. The term "pulley" as used throughout this document is defined as including a rotatable wheel along which a cable may move.

The apparatus, system, and method of the present invention is particularly useful for performing neurosurgical procedures, such as stereotaxy, and endoscopic procedures, such as laparoscopy, arthroscopy, thoracoscopy and the like. Furthermore, the present invention is particularly useful as part of a telerobotic surgical system that allows the surgeon to manipulate the surgical instruments through a servomechanism at a location remote from the patient. One example of a robotic surgical system is the da Vinci® S™ surgical system available from Intuitive Surgical, Inc. of Sunnyvale, Calif. A User's Guide for the da Vinci® S™ surgical system is available from Intuitive Surgical, Inc. and is incorporated by reference herein for all purposes.

Figure 2A:
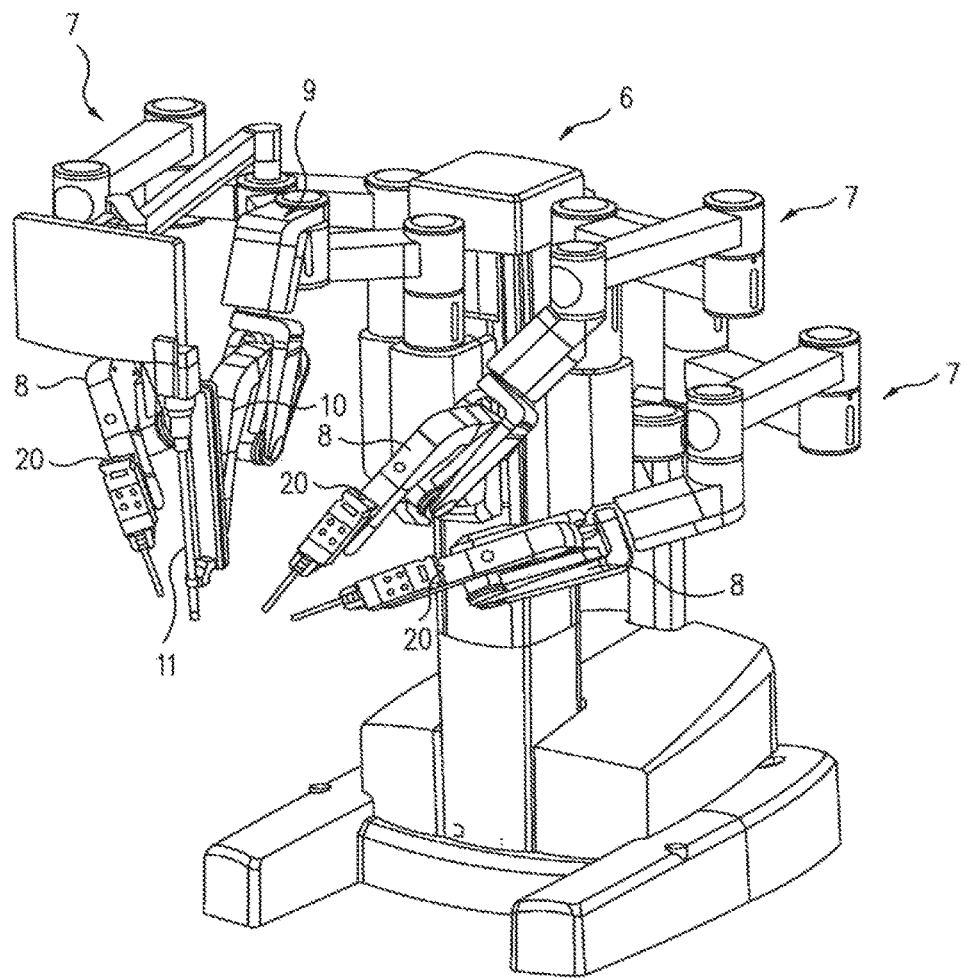
FIGS. 2A and 2B illustrate a perspective view and a front view, respectively, of an embodiment of a manipulator system, including positioning linkages or set up joints which allow a patient side robotic manipulator and/or an endoscope or camera robotic manipulator to be pre-configured for surgery.
Figure 2B:
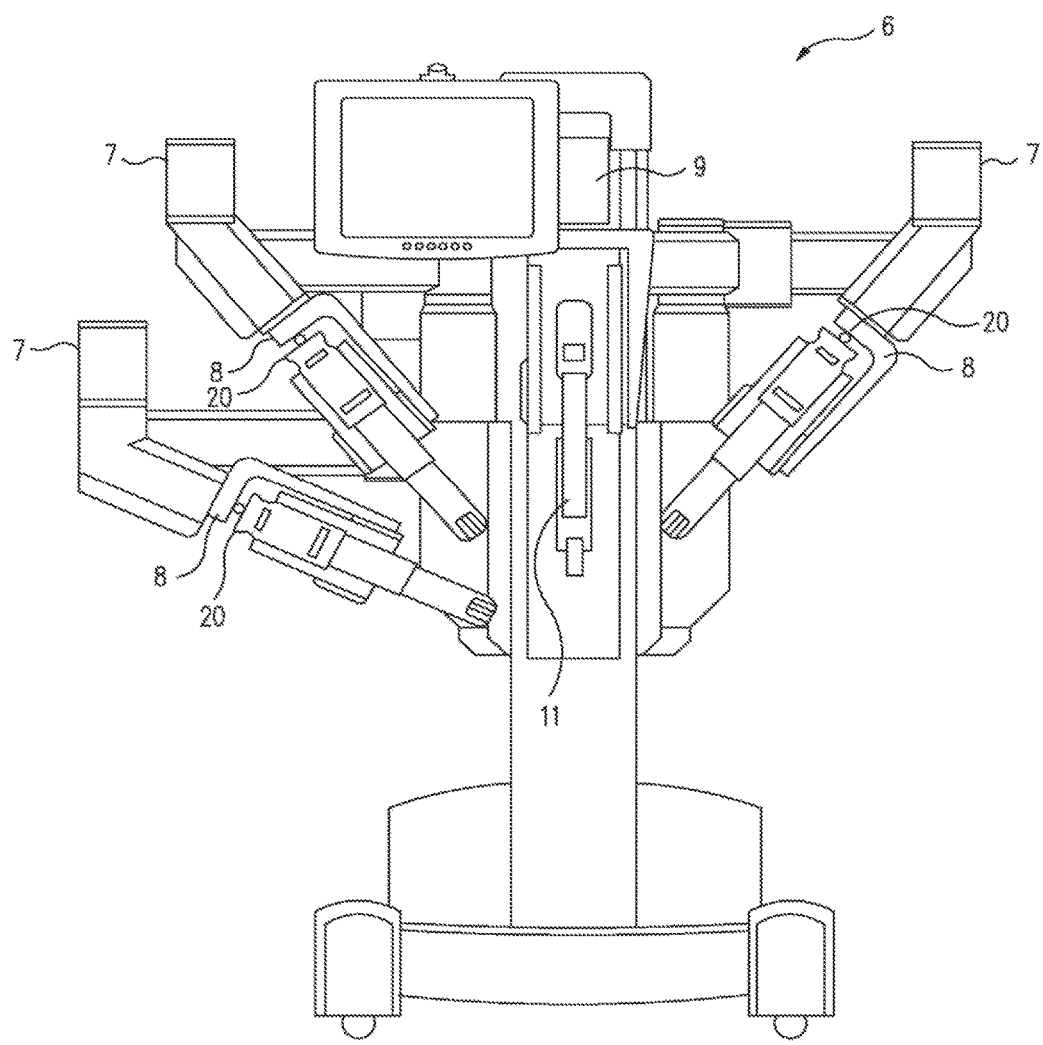
Figure 3:
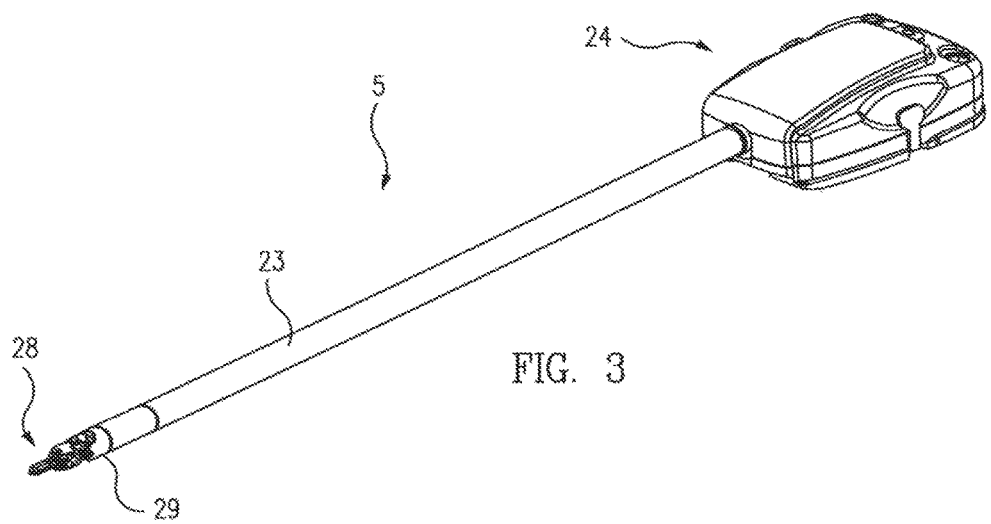
FIG. 3 is a perspective view of an example of a surgical instrument for use in the system of FIG. 1.

FIGS. 1-3 illustrate components of a robotic surgical system 1 for performing minimally invasive robotic surgery. System 1 is similar to that described in more detail in U.S. Pat. No. 6,246,200, the full disclosure of which is incorporated herein by reference. A system operator O (generally a surgeon) performs a minimally invasive surgical procedure on a patient P lying on an operating table T. The system operator O sees images presented by display 12 and manipulates one or more input devices or masters 2 at a surgeon's console 3. In response to the surgeon's input commands, a computer processor 4 of console 3 directs movement of surgical instruments or tools 5, effecting servomechanical movement of the instruments via a robotic patient-side manipulator system 6 (a cart-based system in this example) including joints, linkages, and manipulator arms each having a telescopic insertion axis. In one embodiment, processor 4 correlates the movement of the end effectors of tools 5 so that the motions of the end effectors follow the movements of the input devices in the hands of the system operator O.

Processor 4 will typically include data processing hardware and software, with the software typically comprising machine-readable code. The machine-readable code will embody software programming instructions to implement some or all of the methods described herein. While processor 4 is shown as a single block in the simplified schematic of FIG. 1, the processor may comprise a number of data processing circuits, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein.

In one example, manipulator system 6 includes at least four robotic manipulator assemblies. Three linkages 7 (mounted at the sides of the cart in this example) support and position manipulators 8 with linkages 7 in general supporting a base of the manipulators 8 at a fixed location during at least a portion of the surgical procedure. Manipulators 8 move surgical tools 5 for robotic manipulation of tissues. One additional linkage 9 (mounted at the center of the cart in this example) supports and positions manipulator 10 which controls the motion of an endoscope/camera probe 11 to capture an image (preferably stereoscopic) of the internal surgical site. The fixable portion of positioning linkages 7, 9 of the patient-side system is sometimes referred to herein as a "set-up arm".

In one example, the image of the internal surgical site is shown to operator O by a stereoscopic display 12 in surgeon's console 3. The internal surgical site is simultaneously shown to assistant A by an assistance display 14.

Assistant A assists in pre-positioning manipulator assemblies 8 and 10 relative to patient P using set-up linkage arms 7, 9; in swapping tools 5 from one or more of the surgical manipulators for alternative surgical tools or instruments 5'; in operating related non-robotic medical instruments and equipment; in manually moving a manipulator assembly so that the associated tool accesses the internal surgical site through a different aperture, and the like.

In general terms, the linkages 7, 9 are used primarily during set-up of patient-side system 6, and typically remain in a fixed configuration during at least a portion of a surgical procedure. Manipulators 8, 10 each comprise a driven linkage which is actively articulated under the direction of surgeon's console 3. Although one or more of the joints of the set-up arm may optionally be driven and robotically controlled, at least some of the set-up arm joints may be configured for manual positioning by assistant A.

Some of the manipulators include a telescopic insertion axis 100 in accordance with an embodiment of the present invention, although in other embodiments, all of the manipulators may include a telescopic insertion axis 100. Telescopic insertion axis 100 allows for movement of mounted instrument 5, via three operably coupled links in one example.

For convenience, a manipulator such as manipulator 8 that is supporting a surgical tool used to manipulate tissues is sometimes referred to as a patient-side manipulator (PSM), while a manipulator 10 which controls an image capture or data acquisition device such as endoscope 11 may be referred to as an endoscope-camera manipulator (ECM). The manipulators may optionally actuate, maneuver and control a wide variety of instruments or tools, image capture devices, and the like which are useful for surgery.

Instruments 5 and endoscope 11 may be manually positioned when setting up for a surgical procedure, when reconfiguring the manipulator system 6 for a different phase of a surgical procedure, when removing and replacing an instrument with an alternate instrument 5', and the like. During such manual reconfiguring of the manipulator assembly by assistant A, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 8 (e.g., a clutch button/switch 103 in FIGS. 6A-6C), or some other component to the manipulator assembly, thereby allowing assistant A to change the manipulator mode.

As can be seen in FIGS. 1 and 2A-2B, indicators 20 may be disposed on a manipulator assembly. In this embodiment, indicators 20 are disposed on manipulators 8 near the interface between the manipulators and their mounted tools 5. In alternative embodiments, indicators 20 may instead be disposed on set-up joints 7, 9, on tools 5, elsewhere on manipulators 8, 10, or the like. An example of an indicator is disclosed in U.S. application Ser. No. 11/556,484, filed Nov. 3, 2006, the full disclosure of which (including all references incorporated by reference therein) is incorporated by reference herein for all purposes.

FIG. 3 illustrates a perspective view of an articulated surgical tool or instrument 5. Tool 5 has a proximal housing 24 which interfaces with a tool holder or instrument interface of the manipulator, generally providing a quick release mounting engagement through a sterile adapter or interface, an example of which is disclosed in U.S. patent application Ser. No. 11/314,040, filed Dec. 20, 2005, and U.S. patent application Ser. No. 11/395,418, filed Mar. 31, 2006, which are incorporated by reference herein for all purposes. Tool 5 includes an elongated shaft 23 supporting an end effector 28 relative to proximal housing 24. Proximal housing 24 accepts and transmits drive signals or drive motion between the manipulator 8 and the end effector 28. An articulated wrist 29 may provide two degrees of freedom of motion between end effector 28 and shaft 23, and the shaft may be rotatable relative to proximal housing 24 about the axis of the shaft so as to provide the end effector 28 with three orientational degrees of freedom within the patient's body.

The surgical tool may include a variety of articulated end effectors, such as jaws, scissors, graspers, needle holders, micro-dissectors, staple appliers, tackers, suction irrigation tools, and clip appliers, that may be driven by wire links, eccentric cams, push-rods, or other mechanisms. In addition, the surgical tool may comprise a non-articulated instrument, such as cutting blades, probes, irrigators, catheters or suction orifices. Alternatively, the surgical tool may comprise an electrosurgical probe for ablating, resecting, cutting or coagulating tissue. Examples of applicable adaptors, tools or instruments, and accessories are described in U.S. Pat. Nos. 6,331,181, 6,491,701, and 6,770,081, the full disclosures of which (including disclosures incorporated by reference therein) are incorporated by reference herein for all purposes. Applicable surgical instruments are also commercially available from Intuitive Surgical, Inc. of Sunnyvale, Calif.

Figure 4:
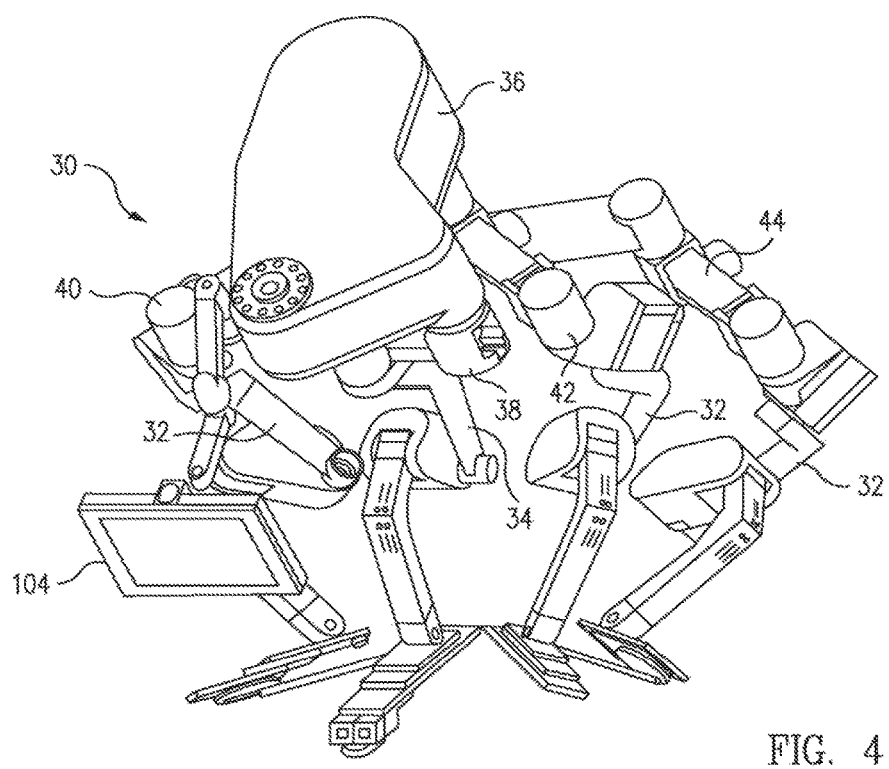
FIG. 4 is a perspective from above of an alternative manipulator system including a plurality of positioning linkages, each supporting a manipulator arm.

Referring now to FIG. 4, a perspective view is illustrated of an alternative modular manipulator support assembly 30 that may be mounted to a ceiling of an operating room. The modular manipulator support 30 aligns and supports a robotic manipulator system relative to a set of desired surgical incision sites in a patient's body. Modular manipulator support 30 generally includes an orientating platform 36 and a plurality of configurable set-up linkage arms 38, 40, 42, 44 that may be coupled to the orienting platform. Each arm movably supports an associated manipulator 32, 34, which in turn movably supports an associated tool or an image capture device. Orienting platform 36 also supports an assistant display 104, which may be used for set-up, instrument changes, viewing of the procedure, and the like. The structures and use of any of the components of modular manipulator support assembly 30 are analogous to those described above regarding manipulator system 6, and are more fully described in co-pending U.S. patent application Ser. No. 11/043,688, filed on Jan. 24, 2005, and entitled "Modular Manipulator Support For Robotic Surgery", the full disclosure of which is incorporated herein by reference. As generally described above, each manipulator 32, 34 of modular manipulator support 30 may also include an insertion axis 100.

Referring now to FIGS. 5A-5E, manipulator 8 including a telescopic insertion axis 100 and a cable tensioning apparatus is shown in more detail in accordance with embodiments of the present invention. The insertion axis of the present invention is comprised of a 3-stage telescopic linear axis including three links, in one example, movably coupled to one another via rails, pulleys, and cables, with the links narrowing in width or form factor moving from the proximal link toward the distal link. Advantageously, the present invention provides for one-handed port and instrument clutching, a larger range of motion, a narrower insertion arm, and greater insertion axis stiffness and strength with reduced inertia as a function of insertion depth, thereby helping to enable a two-quadrant surgery with a single setup (e.g., a colorectal surgery), and providing for more space and visibility near the surgical field.

Figure 5B:
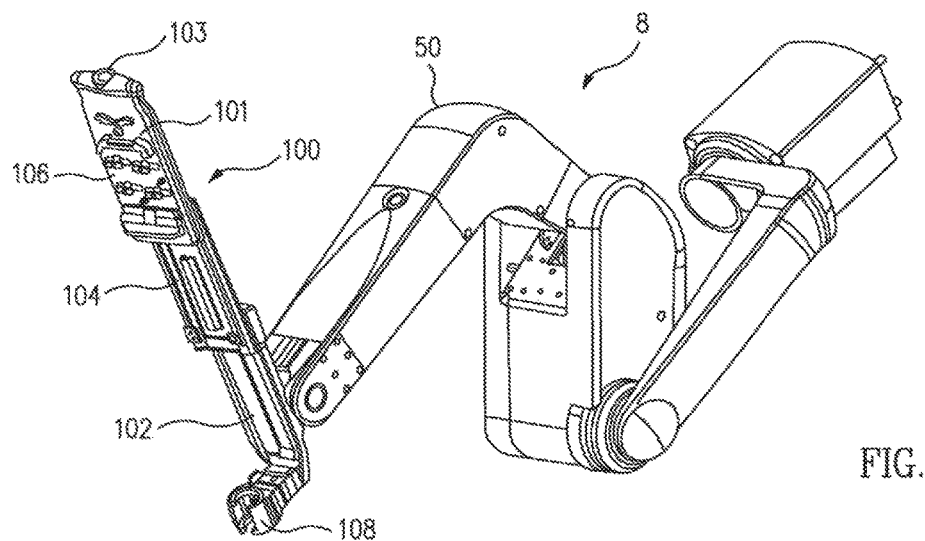
Figure 5C:
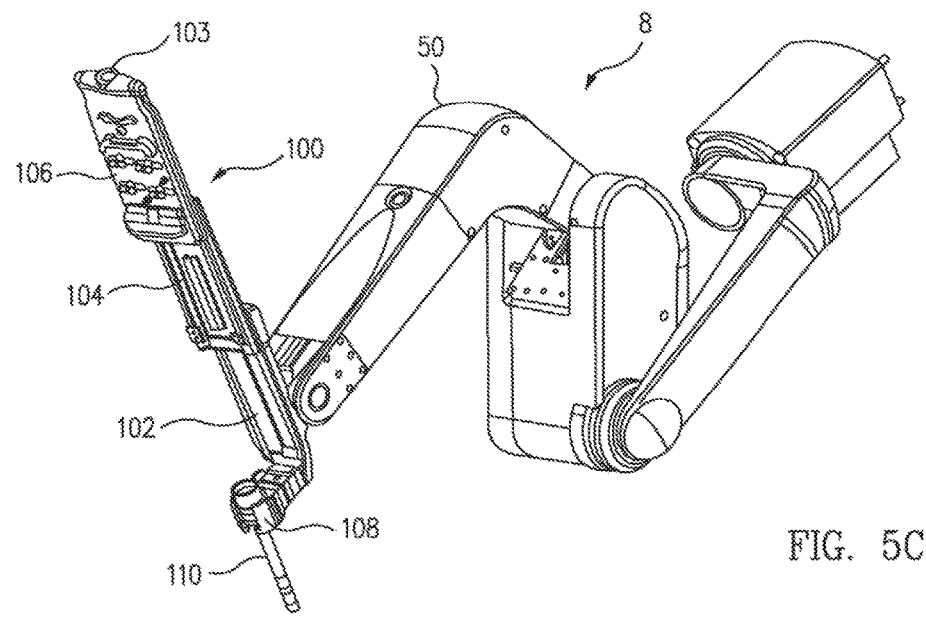
Figure 5D:
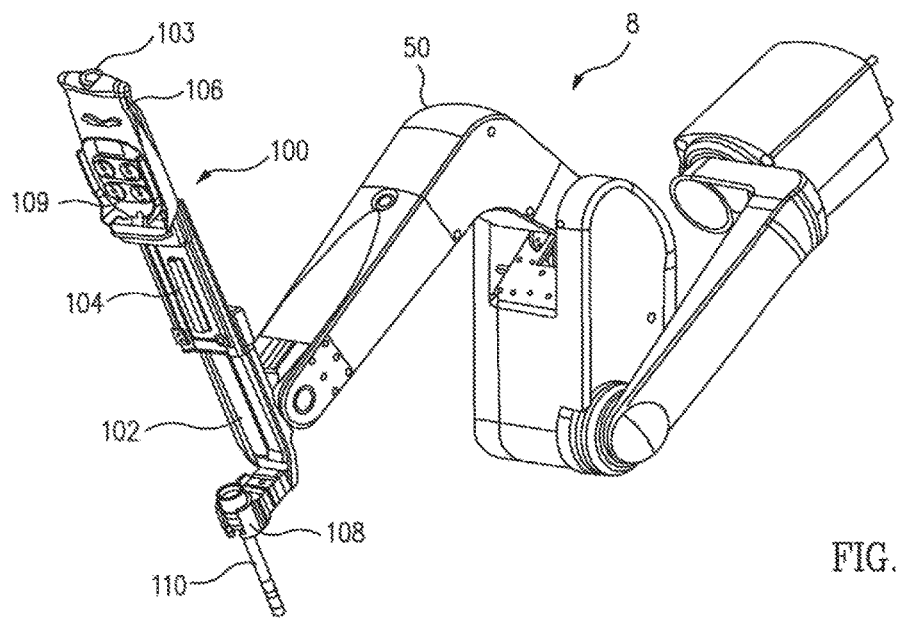
Figure 5E:
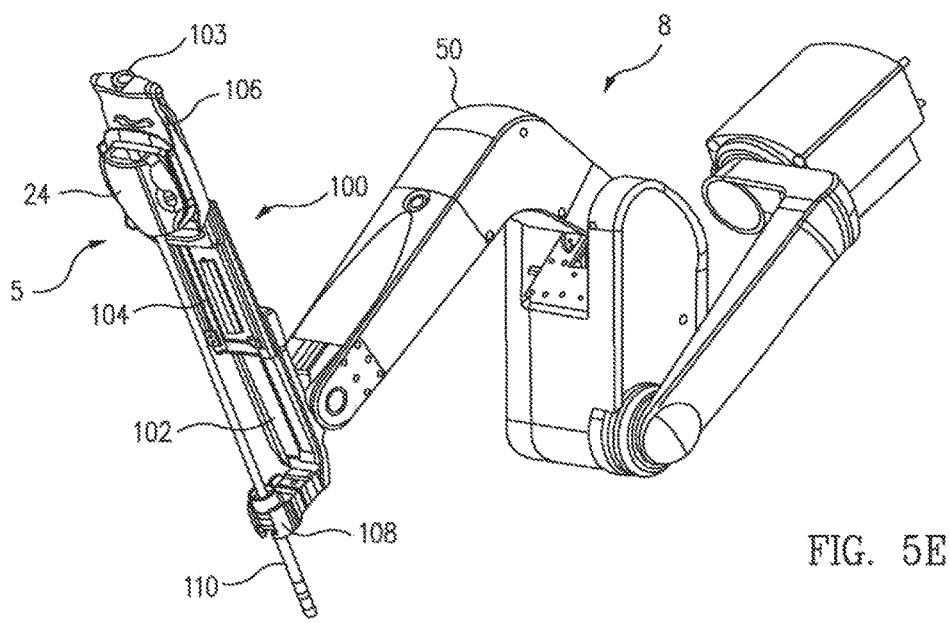

FIGS. 5A through 5E illustrate a perspective view of manipulator 8 including a manipulator arm 50, and telescopic insertion axis 100 operably coupled to a distal end of arm 50 in accordance with an embodiment of the present invention. Telescopic insertion axis 100 includes a first link or base link 102, a second link or idler link 104 operably coupled to base link 102, and a third link or carriage link 106 operably coupled to idler link 104. FIG. 5A1 illustrates a closer view of carriage link 106.

Base link 102 is operably coupled to a distal end of a manipulator arm 50, and in one example has an accessory clamp 108 attached to a distal end of base link 102. An accessory 110, such as a cannula, may be mounted onto accessory clamp 108. An example of applicable accessory clamps and accessories are disclosed in pending U.S. application Ser. No. 11/240,087, filed Sep. 30, 2005, the full disclosure of which is incorporated by reference herein for all purposes. An example of applicable sterile adaptors and instrument housings are disclosed in U.S. application Ser. No. 11/314,040, filed Dec. 20, 2005 and in U.S. application Ser. No. 11/395,418, filed Mar. 31, 2006, the full disclosures of which are incorporated by reference herein for all purposes.

Carriage link 106 includes an instrument interface 101 for operably coupling to a sterile adaptor 109, that is capable of being operably coupled to a housing of an instrument (e.g., housing 24 of FIG. 3). In one embodiment, the sterile adaptor is part of a drape that may be draped over the robotic surgical system, and in particular the manipulator system, to establish a sterile barrier between the non-sterile PSM arms and the sterile field of the surgical procedure. An example of an applicable drape and adaptor is disclosed in pending U.S. application Ser. No. 11/240,113, filed Sep. 30, 2005, the full disclosure of which is incorporated by reference herein for all purposes.

Idler link 104 is movably coupled between base link 102 and carriage link 106 to allow the links 102, 104, and 106 to move relative to one another along a lengthwise axis in a telescoping fashion.

Figures 6A, 6B, 6C:
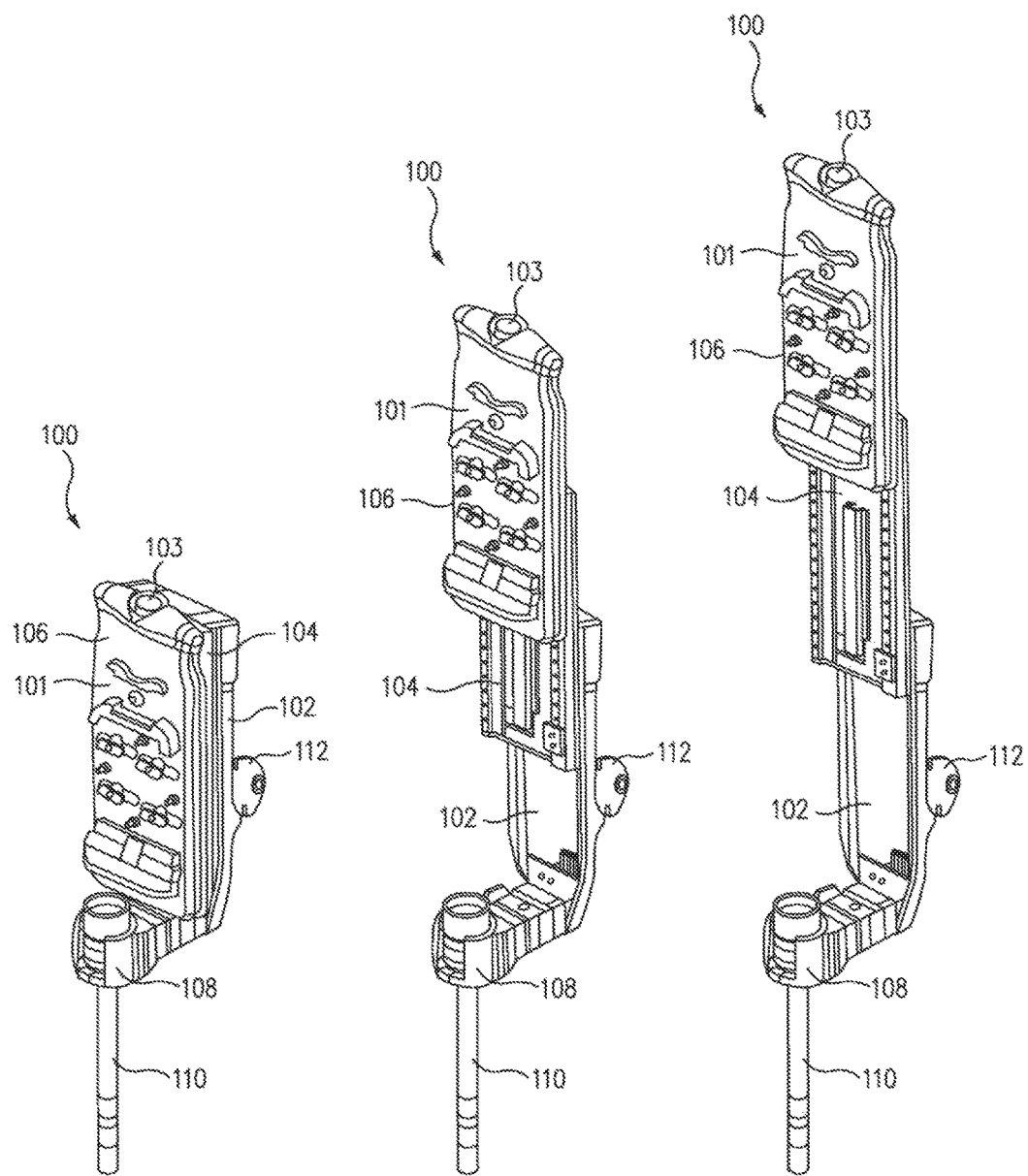
FIGS. 6A through 6C are perspective views of the insertion axis, an accessory mount (e.g., a cannula mount), and an accessory (e.g., a cannula), the insertion axis being telescoped from a retracted position in FIG. 6A, to an intermediate position in FIG. 6B, and to a fully extended position in FIG. 6C.

FIGS. 6A through 6C are perspective views of the insertion axis 100, accessory mount 108 (e.g., a cannula mount), and an accessory 110 (e.g., a cannula) but not including an instrument or an instrument adaptor, the insertion axis 100 being telescoped from a retracted position in FIG. 6A, to an intermediate position in FIG. 6B, and to a fully extended position in FIG. 6C. A pulley bank 112 is located on an underside of base link 102 for passing cables and electrical wires between insertion axis 100 and manipulator arm 50 of manipulator system 6.

Motion along axes C through G in manipulator 8, as shown in FIGS. 5A and 5A1, are provided by cables extending between the proximal and distal links in accordance with the present invention. The robotic arm can then control a tool operably coupled to the arm. The cables are a component of a transmission system also including drive pulleys, idler pulleys, and output pulleys, which are driven by electric motors. A pulley bank is located on an underside of base link 102 for passing cables between insertion axis 100 and manipulator arm 50 of manipulator system 6. A plurality of motion feed-throughs, in addition to other elements, may also be provided for transferring motion.

The drive assembly may further include a plurality of drive motors coupled to the arm for rotation therewith. Yaw and pitch motors control the motion of the arm about the A axis and the B axis (FIG. 5A), respectively, and drive motors control the motion of the wrist unit and surgical tool. In one embodiment, four drive motors are mounted proximally in the arm to control four degrees of freedom to the tool mounted distally on the arm (the D, E, F, and G axes). Also, a proximally mounted motor controls the insertion position of the tool distally on the arm (along the C axis). The drive motors will preferably be coupled to encoders and potentiometers (not shown) to enable the servomechanism. Embodiments of the drive assembly, arm, and other applicable parts are described for example in U.S. Pat. Nos. 6,331,181, 6,491,701, and 6,770,081, the full disclosures of which (including disclosures incorporated by reference therein) are incorporated herein by reference for all purposes. The manipulator arm and the drive assembly may also be used with a broad range of positioning devices. A more complete description of a remote center positioning device can be found in U.S. patent application Ser. No. 08/504,301, filed Jul. 20, 1995, now U.S. Pat. No. 5,931,832, the complete disclosure of which is incorporated herein by reference for all purposes.

To get power and signals to and from a printed circuit assembly (PCA) in carriage link 106, a wire harness may be used. In one embodiment, the remote PCA may have inputs and outputs for providing power and/or communicating with LEDs, Hall effect sensors, a sterile adaptor, an instrument, and a user interface button (e.g., for a clutch operation). The remote PCA may also include an input for receiving power and an input/output for communicating with a main PCA (e.g., processor 4 of FIG. 1). In one embodiment, the main PCA may have inputs and outputs for providing power and/or communicating with motors (e.g., the main PCA transmits position controls to the motors and processes potentiometer and encoder signals), sensors, the user interface button, the remote PCA, and other printed circuit boards on a patient side cart system via a serial communication bus. An example of the inputs and outputs of applicable PCAs are described in U.S. application Ser. No. 11/613,915, filed Dec. 20, 2006, entitled "Wireless Communication In A Robotic Surgical System", the complete disclosure of which has been previously incorporated herein by reference for all purposes. The remote PCA may include, in one example, an Embedded Serializer for Instrument Interface (ESII) PCA, and the main PCA may include, in one example, an Embedded Serializer Patient Manipulator (ESPM) PCA, both available from Intuitive Surgical, Inc. of Sunnyvale, Calif.

Referring now to FIGS. 7A-7B and 8A-8B, tensioning schemes for a closed loop cable drive used for a wrist axis and an insertion axis of the manipulator arm, respectively, are illustrated in accordance with an embodiment of the present invention.

Figure 7A:
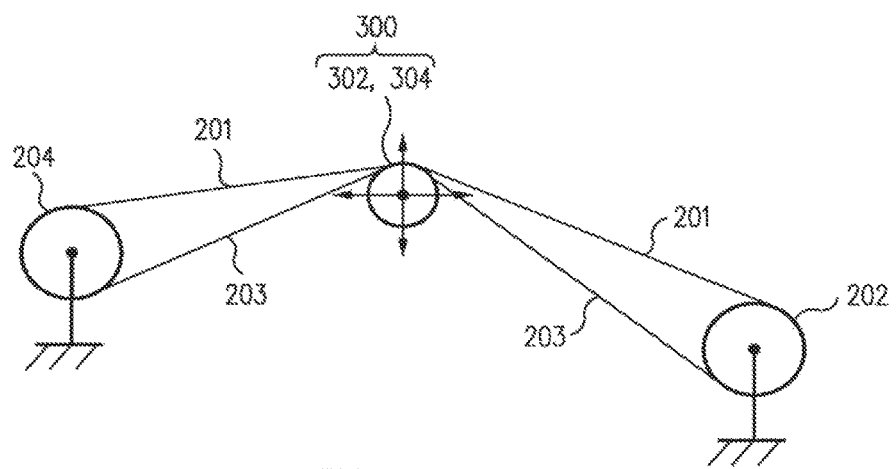
FIGS. 7A and 7B illustrate a side view and a perspective view, respectively, of a closed loop cable tensioning scheme for a wrist axis of a manipulator arm in accordance with an embodiment of the present invention.
Figure 7B:
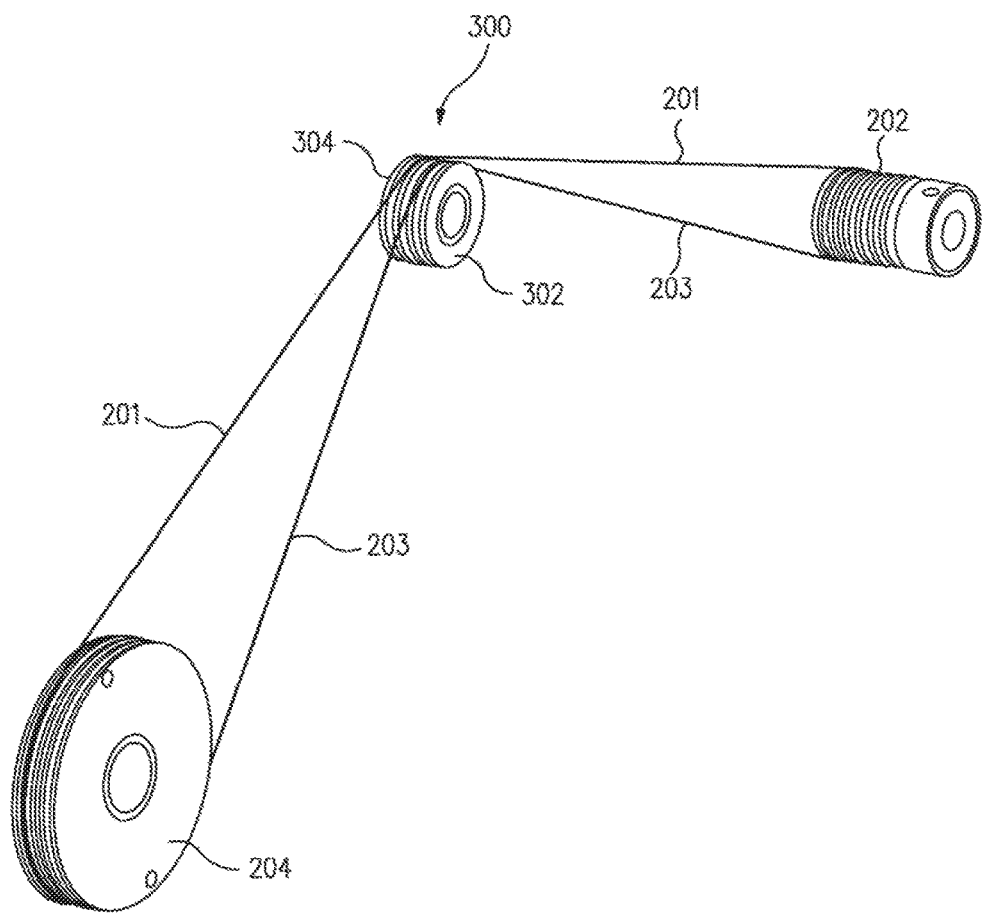

In FIGS. 7A and 7B, cables may extend from a pulley 202 coupled to a motor, which will be referred to as a capstan throughout this document, and over an adjustable idler pulley set 300 including two pulleys 302 and 304 within the manipulator arm (pulleys 302 and 304 are positioned in parallel along an axis perpendicular to the page and therefore appear as one pulley in FIG. 7A). Cables 201 and 203 each extend around an output pulley 204 at the distal end of the arm, and over idler pulleys 302 and 304, respectively, back to the capstan 202. In one embodiment, cables 201 and 203 are anchored to the capstan 202 as well as the output pulley 204 via ball crimps on the cable and slots in the pulleys. One cable is used to form each side of the closed loop (e.g., cable 201 on top and cable 203 on the bottom), and thus two cables are required for a single closed loop axis drive. In one example, cables 201 and 203 run from capstan 202 to output pulley 204, passing over idler pulleys 302 and 304, respectively, to route the cables through the joints and internal cavities of the manipulator arm. It is noted that cables 201 and 203 may pass over a plurality of idler pulleys 300 in some embodiments.

In one embodiment, the method of tensioning the cables is achieved by altering the position of two of the idler pulleys between the anchor points: one idler pulley on each side of the closed loop. These idler pulleys can be moved in either a linear or rotary fashion, or both, relative to their mounting, as long as the overall length of the closed loop cable path changes as a function of their position. Examples of applicable idler pulleys are further discussed below with respect to FIGS. 11A-11C and 13A-13C.

Figure 8A:
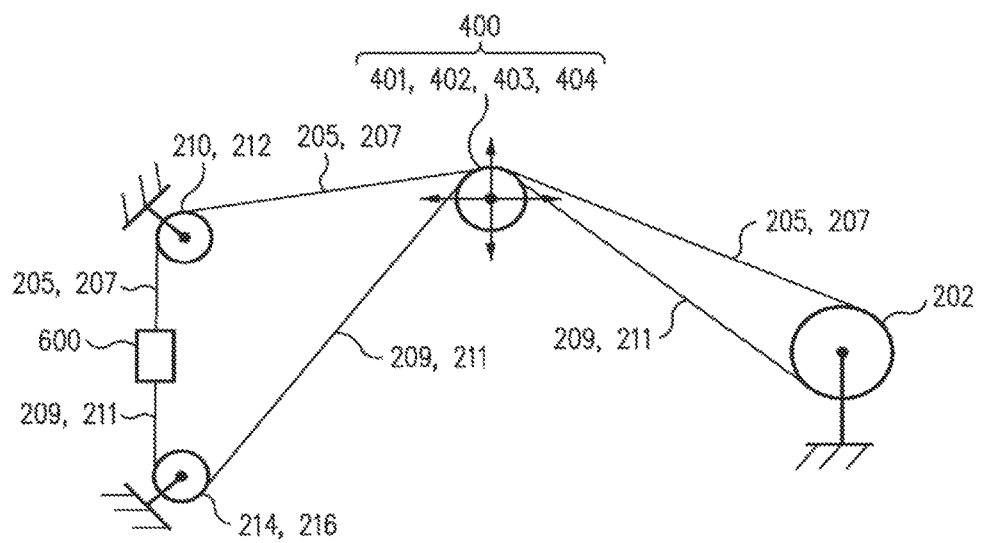
FIGS. 8A and 8B illustrate a side view and a perspective view, respectively, of a closed loop cable tensioning scheme for an insertion axis of a manipulator arm in accordance with another embodiment of the present invention.
Figure 8B:
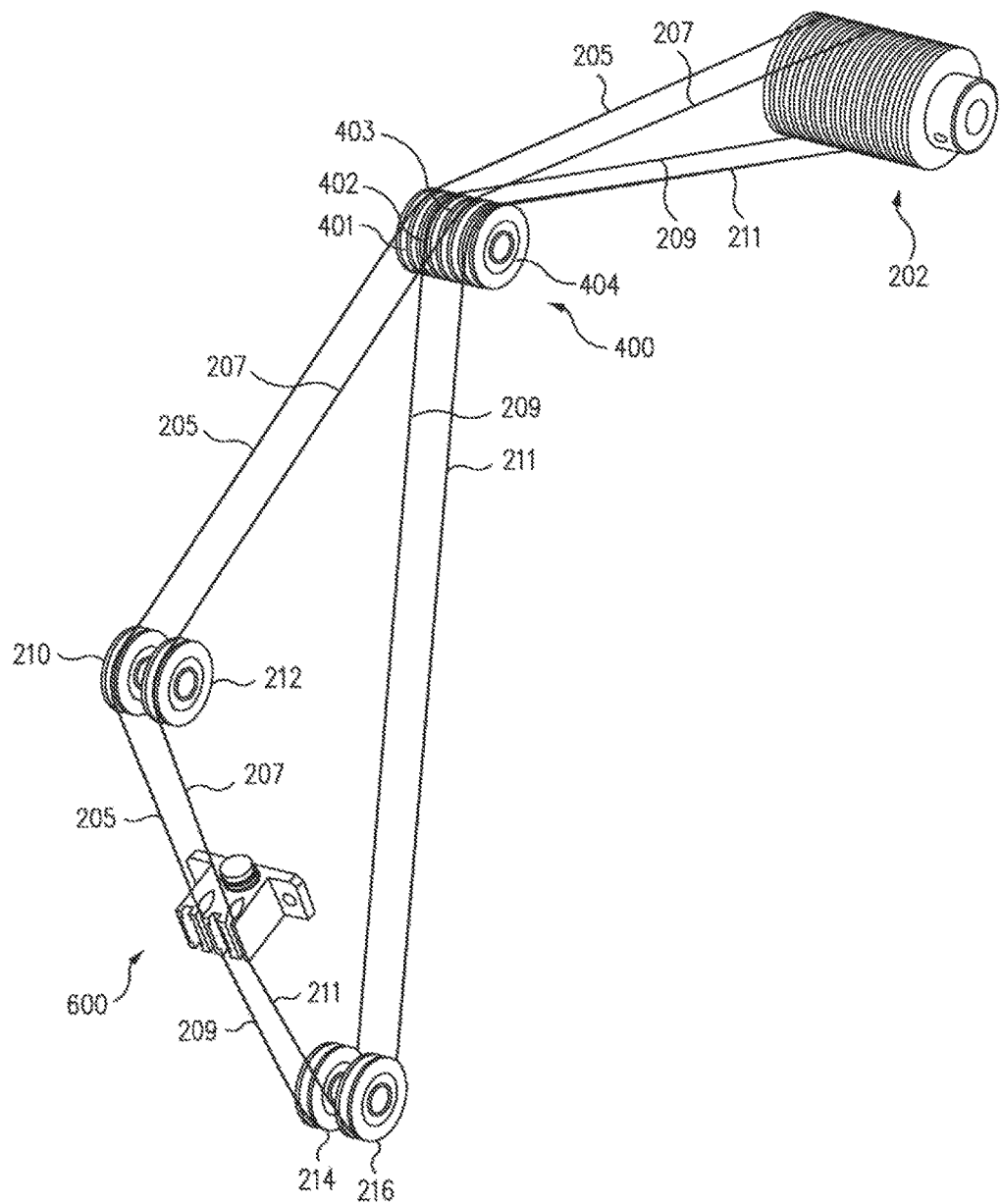

Referring now to FIGS. 8A and 8B in accordance with another embodiment (e.g., in the insertion axis), cables 205, 207, 209, and 211 are anchored to capstan 202 and a termination block 600 that is fastened to one of the links (e.g., idler link 104) that comprises the linear carriage on the distal end of the arm. Similar to the embodiment described above with respect to FIG. 7, one continuous cable is used to form each side of the closed loop, and thus two cables are required for a single closed loop axis drive. One difference between this embodiment and that described above with respect to FIGS. 7A and 7B is that this embodiment uses two parallel cables in each direction of the closed loop to provide a safety feature. Utilizing parallel cables provides redundancy and load sharing, and the termination block 600 is instrumental to enable these safety features. An example of termination block 600 is further discussed below with regard to FIGS. 14A-14D.

Between capstan 202 and termination block 600, cables 205 and 207 in parallel, and cables 209 and 211 in parallel, pass over fixed idler pulleys 210, 212 and 214, 216, respectively, and over an adjustable idler pulley set 400 including four pulleys 401, 402, 403, and 404, used to route the cables through the joints and internal cavities of the robots links. It is noted that cables 205, 207, 209, and 211 may pass over a plurality of idler pulleys 400 in some embodiments.

In one embodiment, a method of tensioning the cables is achieved by altering the position of four of these idler pulleys between the anchor points: two idler pulleys on each side of the closed loop. These idler pulleys can be moved in either a linear or rotary fashion relative to their mounting, as long as the overall length of the closed loop cable path changes as a function of their position. An example of an applicable idler pulley 400 is further discussed below with respect to FIGS. 12A-12C.

Figure 9A:
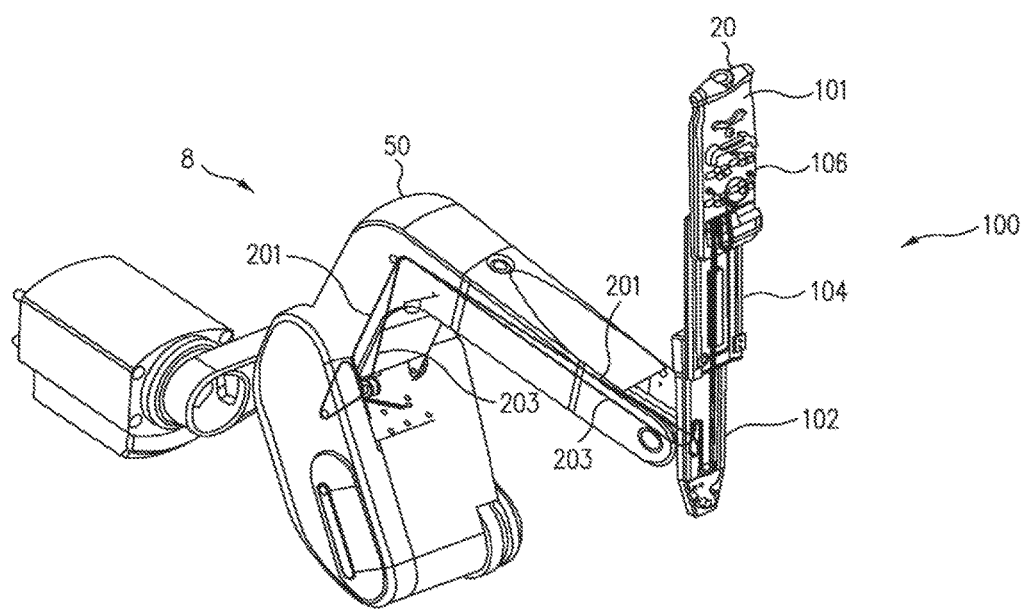
FIG. 9A is a view of a cable running through a manipulator arm and insertion axis in accordance with an embodiment of the present invention.
Figure 9B:
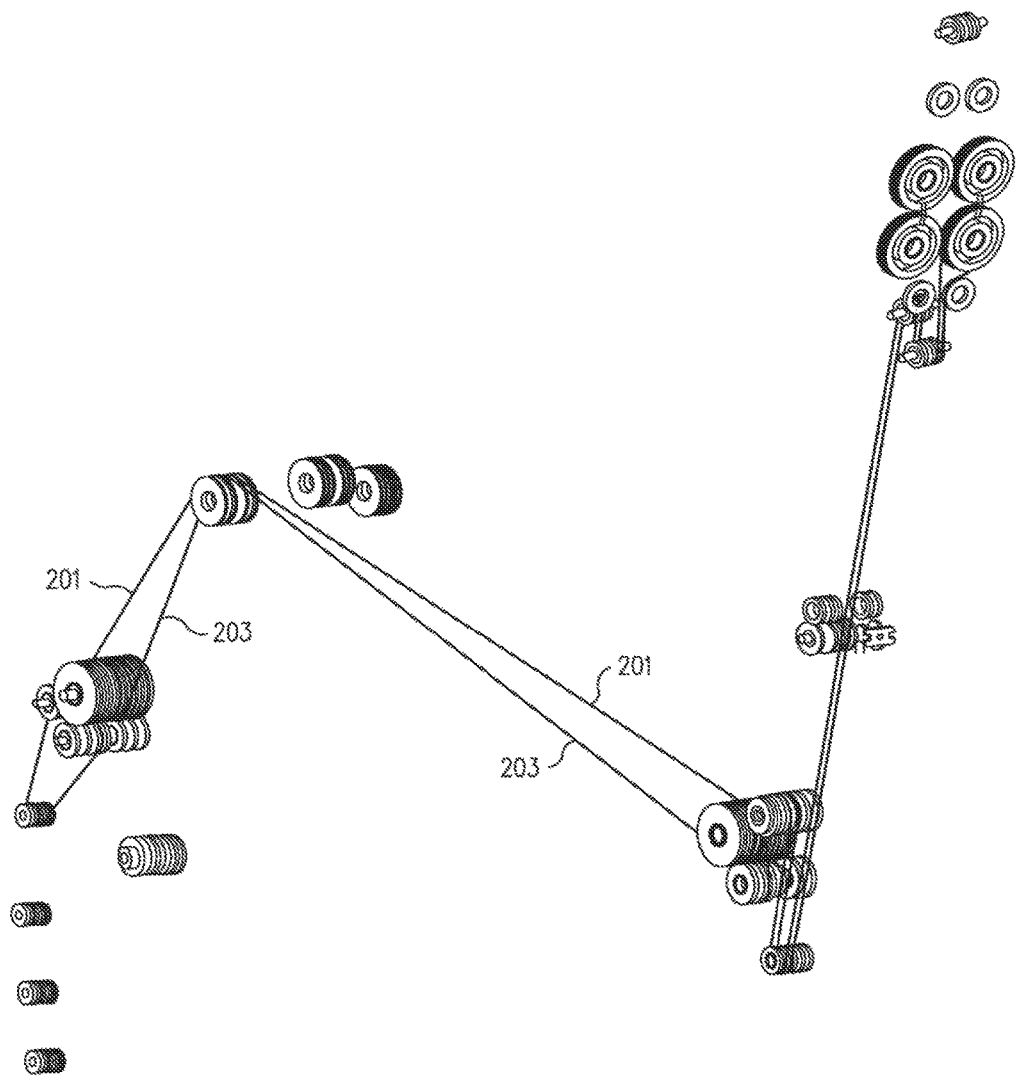
FIGS. 9B and 9C illustrate a perspective view and a side view, respectively, of the cable and pulleys of FIG. 9A in accordance with an embodiment of the present invention.
Figure 9C:
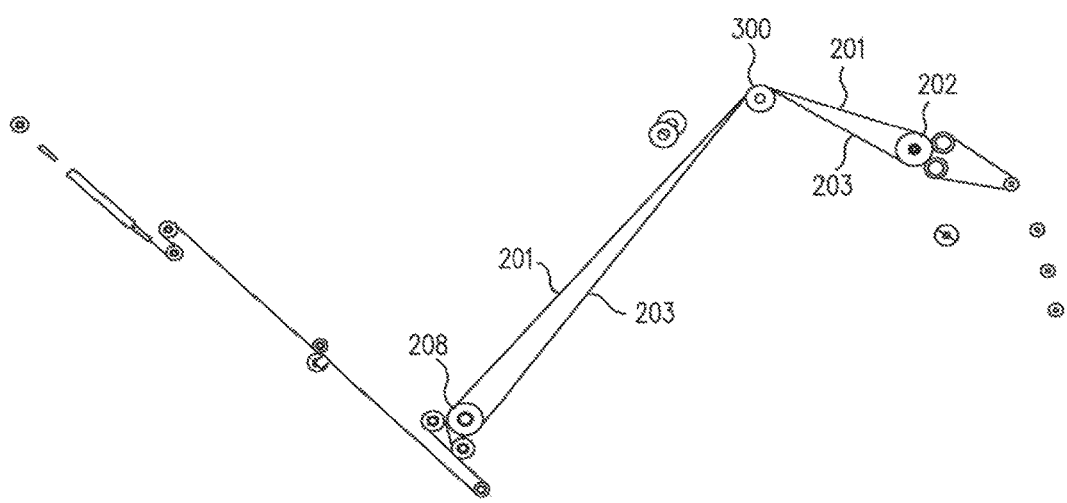
Figure 10A:
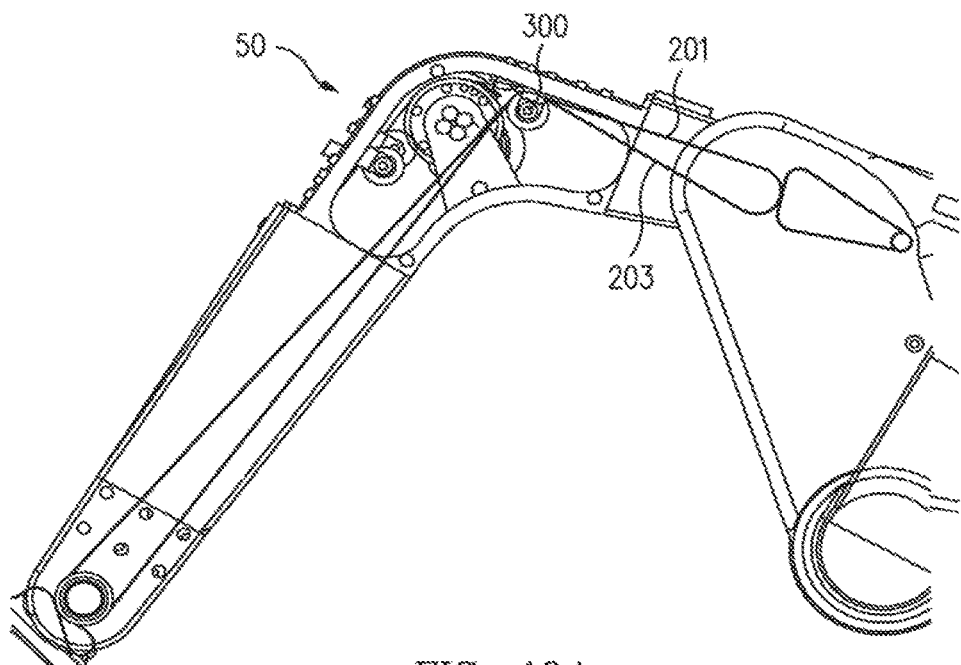
FIGS. 10A and 10B illustrate views of a linear tensioning apparatus within a manipulator arm of a telerobotic surgical system in accordance with an embodiment of the present invention.
Figure 10B:
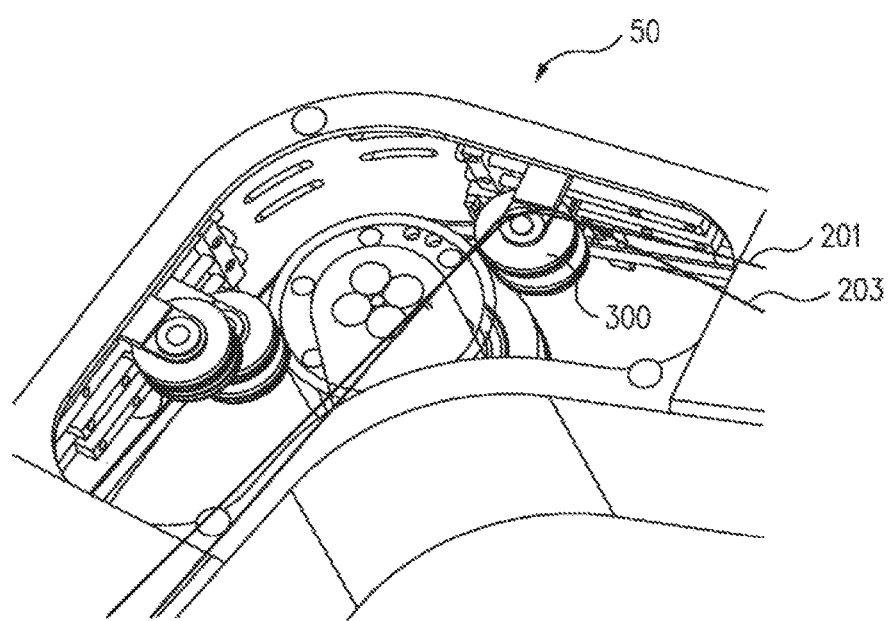
Figure 11D:
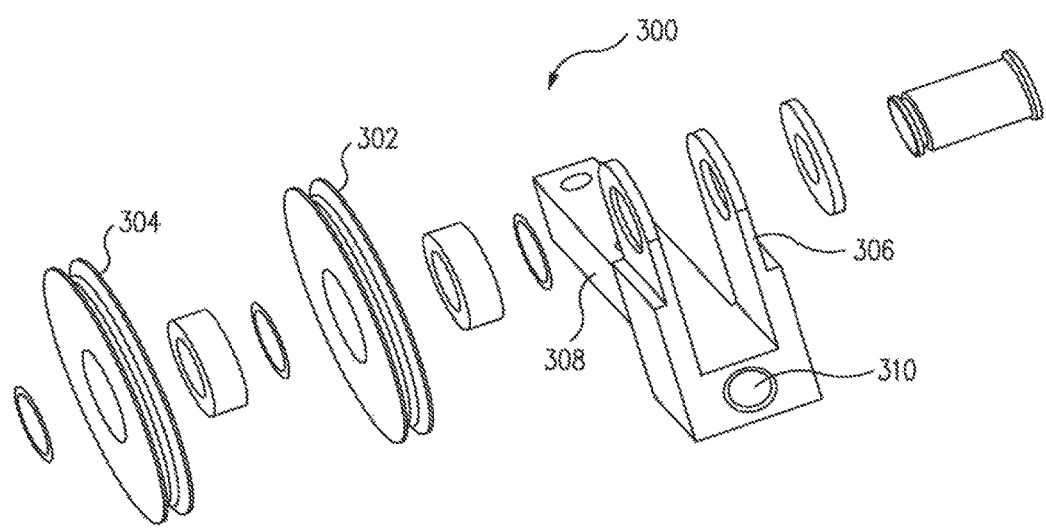

Referring now to FIGS. 9A-9C and 10A-10B, cables 201 and 203 are illustrated running through manipulator 8 in accordance with one embodiment of the present invention. FIG. 9A is a view of cables 201 and 203 running through manipulator arm 50 and insertion axis 100 of a telerobotic surgical system. FIGS. 9B and 9C illustrate a perspective view and a side view, respectively, of the cable and pulleys of FIG. 9A. FIGS. 10A and 10B illustrate closer views of an adjustable idler pulley 300 within manipulator arm 50.

Referring now to FIGS. 11A-11D, different views of an adjustable linear tensioner 300 are shown in accordance with an embodiment of the present invention. Tensioner 300 includes an arm 306, pulleys 302 and 304 rotatably coupled to a first end of arm 306, and a base 308 operably coupled to a second end of arm 306. Pulleys 302 and 304 may rotate independently of each other. In one embodiment, tensioner 300 includes a translation mechanism for changing the position of the pulleys 302, 304 to control a tension of a cable movable along the pulleys. In one example, the translation mechanism includes a threaded cavity 310 for mating with a screw 312 (shown by dashed lines) along which the base 308 may translate, as shown by the double-sided arrow. In other embodiments, base 308 may include a cavity for sliding along a rod. The axial position of screw 312 (or a rod) is fixedly mounted within the manipulator in one embodiment (but may spin along the lengthwise axis of the screw or rod in one example). Tensioner 300 further includes a locking mechanism for maintaining the position of the base 308 relative to screw 312 and therefore to the arm of the robot, thereby maintaining the cable tension of a cable(s) (not shown) running along pulleys 302 and/or 304. The locking mechanism may include in one example a screw 316 or similar fastener for coupling to a threaded cavity 314 in base 308. As shown in the exploded view of tensioner 300 in FIG. 11D, various bearings, shafts, and spacers may be used for allowing pulleys 302 and 304 to rotate.

In this embodiment, two pulleys 302 and 304 are included with either side of a closed loop cable transmission passing over them. The position of these pulleys 302 and 304 are constrained to a linear path and movable by a translation mechanism, in this embodiment threaded cavity 310 and screw 312. Turning screw 312 (in one example with an ordinary screw driver) adjusts the linear position of the pulleys 302, 304 along screw 312. The position of the pulleys in turn adjusts the tension of the cables because the linear path along which the pulleys move is not parallel to the path of the cables (see, for example, FIGS. 10A and 10B). In this design, an end of the closed loop can be around an output pulley (e.g., output pulley 204 of FIG. 7) that is free to spin. The spinning of such an output pulley will eliminate tension imbalance between the two sides of the closed loop. Advantageously, the present invention provides a means to easily adjust the cable tension of a closed loop transmission using two pulleys that move linearly. It is noted that although two pulleys are illustrated as an integrated cable tensioner 300, one or other various numbers of pulleys are within the scope of the present invention.

Referring now to FIGS. 12A-12C, different views of an adjustable linear tensioner 400 are shown in accordance with an embodiment of the present invention. Similar to tensioner 300, tensioner 400 includes an arm 406 having a first end and a second end, pulleys 401, 402, 403, and 404 rotatably coupled to the first end of arm 406, and a base 408 operably coupled to the second end of arm 406. Pulleys 401-404 may rotate independently of each other. In one embodiment, tensioner 400 includes a translation mechanism for changing the position of the pulleys 401-404 to control a tension of a cable(s) movable along the pulleys. In one example, the translation mechanism includes a threaded cavity 410 for mating with a screw 412 (shown by dashed lines) along which the base 408 may translate, as shown by the double-sided arrow. In other embodiments, base 408 may include a cavity for sliding along a rod. The axial position of screw 412 (or rod) is fixedly mounted within the manipulator in one embodiment (but may spin along the lengthwise axis of the screw or rod in one example). Turning screw 412 (in one example with an ordinary screw driver) adjusts the linear position of the pulleys 401-404 along screw 412. The position of the pulleys in turn adjusts the tension of the cables because the linear path along which the pulleys move is not parallel to the path of the cables (see, for example, FIGS. 10A and 10B).

Tensioner 400 further includes a locking mechanism for maintaining the position of the base 408 relative to screw 412 and therefore to the arm of the robot, thereby maintaining the cable tension of a cable(s) (not shown) running along pulleys 401-404. The locking mechanism may include in one example a screw 416 or similar fastener for coupling to a threaded cavity 414 in base 408. It is noted that although four pulleys are illustrated as an integrated cable tensioner 400, one or other various numbers of pulleys are within the scope of the present invention.

Figure 13A:
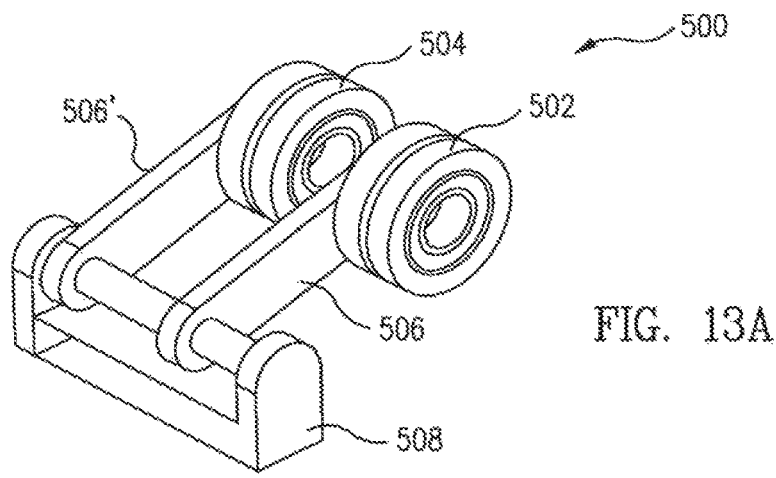
FIGS. 13A through 13C are different views of a rotational tensioning apparatus in accordance with an embodiment of the present invention.
Figure 13B:
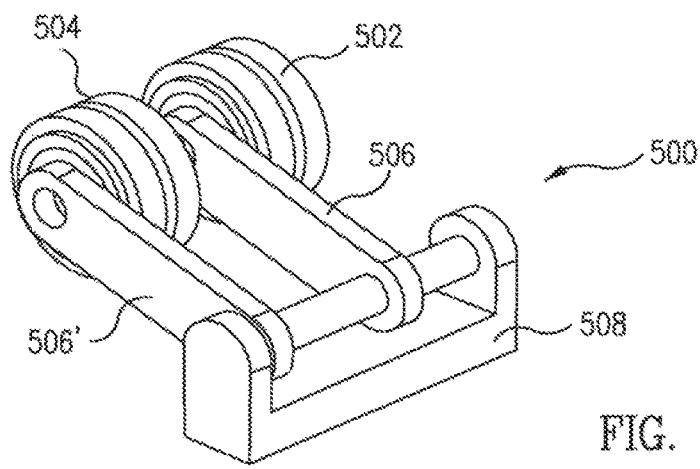
Figure 13C:
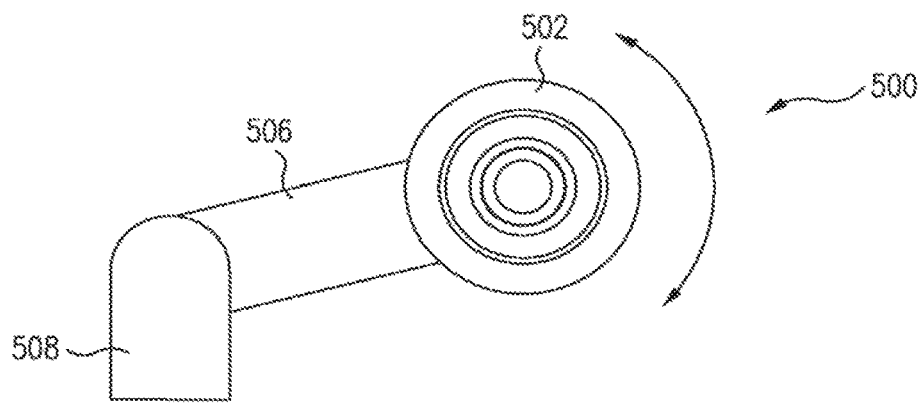

Referring now to FIGS. 13A-13C, different views of an adjustable rotational tensioner 500 are shown in accordance with an embodiment of the present invention. Tensioner 500 includes a base 508, two arms 506 and 506' with each arm having a first end movably coupled to base 508, and two pulleys 502 and 504 operably coupled to a second end of arm 506 and 506', respectively. In one embodiment, pulleys 502 and 504 may rotate independently of each other and arms 506 and 506' may move independently of each other with respect to base 508. Base 508 is fixedly coupled to a position within the manipulator, and arms 506 and 506' are rotatable about base 508 as shown by the double-sided arrow. In one embodiment, arms 506 and 506' are spring loaded by torsion springs in such a way that the spring force is balanced against the cable tension through the pulleys. Therefore, the cable tension is proportional to the strength of the spring.

Figure 13E:
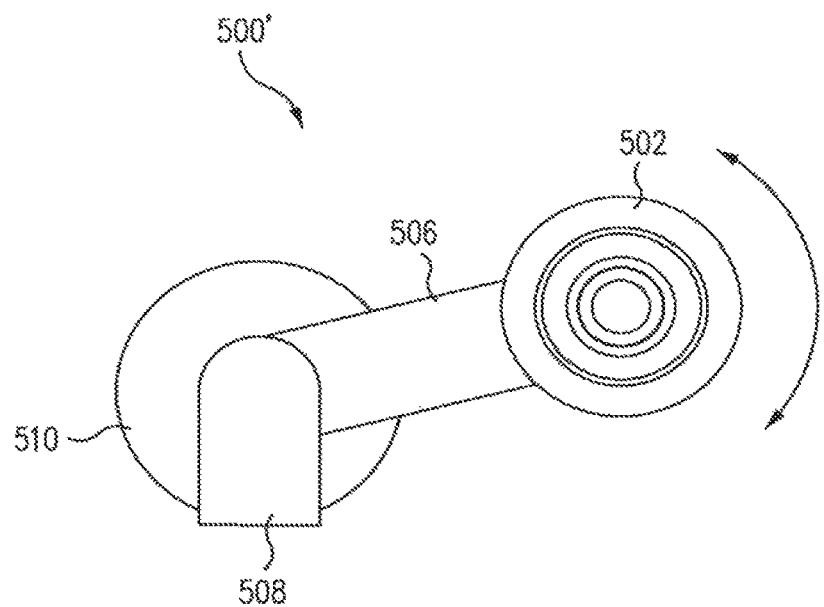
FIGS. 13D and 13E are side views of other rotational tensioning apparatus in accordance with other embodiments of the present invention.
Figure 13D:
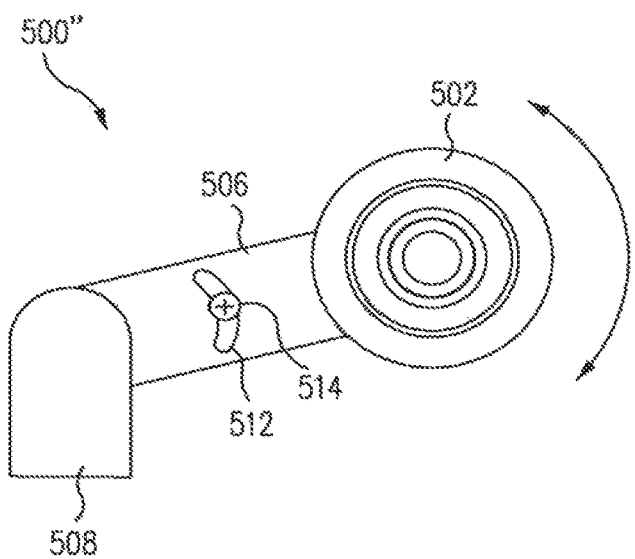
Figure 14A:
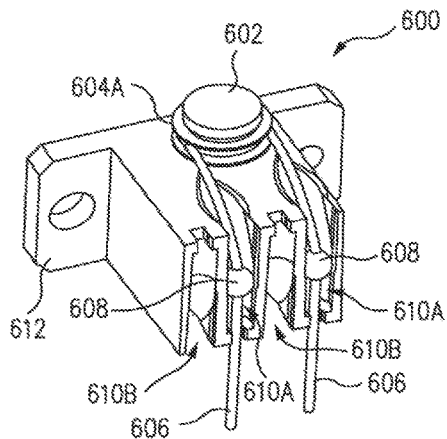
FIGS. 14A through 14D are different views of a termination block in accordance with an embodiment of the present invention.
Figure 14B:
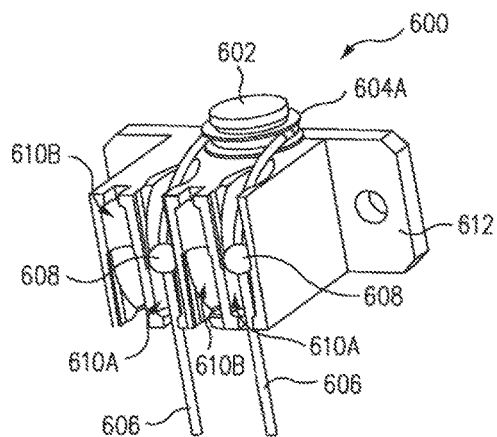
Figure 14C:
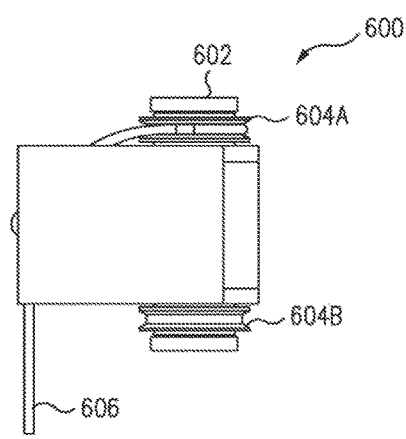
Figure 14D:
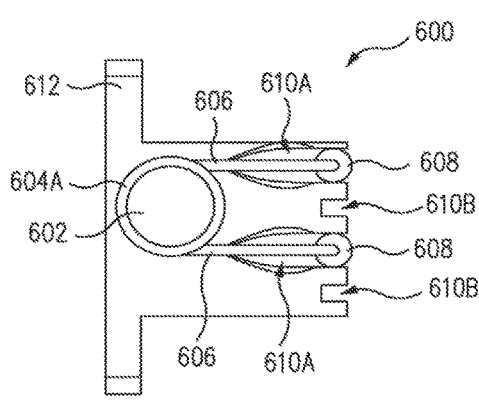

Referring now to FIGS. 13D and 13E, tensioners 500' and 500" are shown further including a locking mechanism for maintaining or locking the position of the first end of arms 506 and 506' with respect to base 508, thereby maintaining the cable tension of a cable(s) (not shown) running along pulleys 502 and/or 504. Once the cable and spring tensions have come to equilibrium, the arms may be locked in place with the locking mechanism (e.g., a screw 514 or similar fastener within an arcuate slot 512 (FIG. 13D) that locks the arms in place and an optional spring washer that may be used for disengaging the locking mechanism and adjusting the cable tension). Alternatively, as shown in FIG. 13E, an electrically engaged brake 510 may be used to lock the arms 506 and 506' automatically, by a processor, such as computer processor 4 of console 3. In one example, brake 510 may be operational when not electrically engaged, and not operational when electrically engaged (or vice versa). The brake could also be engaged pneumatically, or by other means. Advantageously, the present invention allows cable tension to be re-calibrated automatically by a processor. Advantageously, the present invention simplifies the process of setting, maintaining, and adjusting cable tension. It is noted that although two pulleys and arms are illustrated as an integrated cable tensioner 500, one or other various numbers of pulleys and arms are within the scope of the present invention.

Referring now to FIGS. 14A-14D, different views of a termination block assembly 600 are shown in accordance with an embodiment of the present invention. Termination block assembly 600 includes a pin 602, a pulley 604A, a mount 612, slots 610A, and ball fittings 608 crimped on a cable 606 that runs through slots 610A. Pulley 604A is used to equalize the tension in parallel cable paths, and slots 610A are used to catch ball fittings 608 if one side of the transmission should break or lose tension. Mount 612 is used for fixedly attaching the termination block assembly 600 to a position within the manipulator. Ball fittings 608 are crimped onto each parallel path of cable 606 that move in slots 610A machined into termination block assembly 600. Under normal operation, these ball fittings 608 are free to move in their respective slots 610A. If the cable on either side of the parallel path were to break, the ball on the opposite side would catch on the bottom of its slot and maintain its ability to control the axis. Therefore, the termination block assembly 600 enables the parallel cables to provide redundant actuation of the insertion axis.

Pulley 604A on the termination block allows the cable to wrap 180° around its midpoint. This enables a load on only one side of the parallel path to equalize with the other side of the parallel path, thus enabling load sharing between the two parallel paths. This is important because the ability to equally share loading will reduce the maximum load any one length of the cable sees. Furthermore, enabling differential movement between the two sides of the parallel cable eliminates small length differences potentially resulting from tolerance stack ups.

In one embodiment of the present invention, termination block assembly 600 may be used in conjunction with a standard fixed pulley transmission or in conjunction with cable tensioners 300, 400, and 500 as described above to form a closed loop. On one end of the transmission, cables may be terminated into a capstan 202, and on the other end the cables may terminate into block assembly 600.

In alternative embodiments of termination block assembly 600, a second pulley 604B and a second set of slots 610B may be included for receiving another cable to pull in the opposite direction, as shown in FIGS. 14A-14D. In addition, a rotatable or stationary post around which a cable may move can be used instead of a pulley in one example.

Furthermore, the termination block assembly is not limited to slots but various apertures may be used to provide cable pathways that can also retain the ball fittings (e.g., holes large enough to fit the cables and counterbores small enough to retain the ball fittings). In yet another example, the cable pathway through the termination block assembly is not limited to running in a parallel plane to the lengthwise axis of the pulley or pin, but may be along a perpendicular plane from the lengthwise axis of the pulley or pin. In other words, the cables would move along one plane through the termination block assembly.

Advantageously, the present invention provides a redundant cable transmission system thereby providing safe and redundant actuation to a critical axis of a manipulator arm such that if a cable breaks or loses tension, the insertion axis is prevented from falling. Furthermore, an advantageous adjustable tensioner is provided for adjusting the tension of cables in a closed loop. The tensioners, termination blocks, systems, and methods of the present invention provide for the improved setting, maintaining, and adjusting of cables used in a robotic surgical system, thus resulting in greater efficiency and improved accuracy of the system.

Embodiments described above illustrate but do not limit the invention. It should also be understood that numerous modifications and variations are possible in accordance with the principles of the present invention. For example, different numbers of arms and pulleys than that provided in the above embodiments of an adjustable cable tensioner is within the scope of the present invention. Furthermore, the system is not limited to four robotic manipulator assemblies, but may include two or more in other examples. Accordingly, the scope of the invention is defined only by the following claims.

We claim:

1. A system comprising:
    a robotic surgical manipulator that includes a termination assembly of a cabling system, the termination assembly comprising:
        a block including first and second cable pathways sized for receipt of a first cable, the first cable pathway including a first retainer sized to prevent passage of a first fitting coupled to the first cable; and
        a first pulley coupled to the block and around which the first cable is routed.

2. The system of claim 1, wherein the first and second cable pathways are parallel to a lengthwise axis through the first pulley.

3. The system of claim 1, wherein the first and second cable pathways are perpendicular to a lengthwise axis of the first pulley.

4. The system of claim 1, wherein the first pulley is coupled to the block by a post stationary relative to the block.

5. The system of claim 1, wherein the first pulley is coupled to the block by a post rotatable relative to the block.

6. The termination assembly of claim 1, wherein the first and second cable pathways are slots formed in the block.

7. The termination assembly of claim 1, wherein the second cable pathway includes a second retainer sized to prevent passage of a second fitting coupled to the first cable.

8. The system of claim 1 further comprising a second pulley coupled to the block, wherein the block further includes third and fourth cable pathways sized for receipt of a second cable, and wherein the second cable is routed around the second pulley.

9. The termination assembly of claim 8 wherein the first and third cable pathways extend parallel to each other.

10. The termination assembly of claim 1, wherein the first cable pathway comprises a slot, the first retainer comprises a bottom of the slot, the first fitting is free to move in the slot, and the first retainer prevents passage of the first fitting past the bottom of the slot.

11. A robotic surgical system comprising:
    a drive assembly;
    a manipulator arm including a termination block, the termination block including first and second cable pathways and a first pulley, wherein the first cable pathway includes a first retainer; and
    a first cable coupled to transmit motion from the drive assembly to the manipulator arm, the first cable extending through the first and second cable pathways and around the first pulley, wherein a first fitting is coupled to the first cable and is retained in the first cable pathway by the first retainer.

12. The robotic surgical system of claim 11, wherein the first and second cable pathways are parallel to a lengthwise axis through the first pulley.

13. The robotic surgical system of claim 11, wherein the first and second cable pathways are perpendicular to a lengthwise axis through the first pulley.

14. The robotic surgical system of claim 11, wherein the first pulley is coupled to the block by a post stationary relative to the termination block.

15. The robotic surgical system of claim 11, wherein the first pulley is coupled to the block by a post rotatable relative to the termination block.

16. The robotic surgical system of claim 11, wherein the first and second cable pathways are slots formed in the termination block.

17. The robotic surgical system of claim 11, wherein the second cable pathway includes a second retainer sized to prevent passage of a second fitting coupled to the first cable.

18. The robotic surgical system of claim 11 further comprising a second pulley coupled to the termination block, wherein the termination block further includes third and fourth cable pathways sized for receipt of a second cable, and wherein the second cable is routed around the second pulley.

19. A robotic surgical system comprising:
    a termination assembly comprising a first cable slot comprising a bottom, a second cable slot comprising a bottom, and a first pulley; and
    a first cable extending through the first cable slot, around the first pulley, and through the second cable slot, the first cable comprising a first fitting located in the first cable slot between the first pulley and the bottom of the first cable slot, the first cable further comprising a second fitting located in the second cable slot between the first pulley and the bottom of the second cable slot.

20. The robotic surgical system of claim 19, further comprising:
    a second cable;
    wherein the termination assembly further comprises a third cable slot comprising a bottom, a fourth cable slot comprising a bottom, and a second pulley; and
    wherein the second cable extends through the third cable slot, around the second pulley, and through the fourth cable slot, the second cable comprising a third fitting located in the third cable slot between the second pulley and the bottom of the third cable slot, the second cable further comprising a fourth fitting located in the fourth cable slot between the second pulley and the bottom of the fourth cable slot.

* * * * *